(12) United States Patent
Evans et al.

(10) Patent No.: US 7,482,452 B2
(45) Date of Patent: Jan. 27, 2009

(54) PROCESS FOR PREPARING 3-AMINOTHIENOPYRIDONE DERIVATIVES

(75) Inventors: Graham Robert Evans, Newmarket (GB); Ian Harold Smith, Kings Langley (GB); Neil Tremayne, Cambridge (GB); Leighton Jones, Cambridge (GB); Marianne Langston, Cambridge, MA (US)

(73) Assignee: Celltech R&D Limited, Slough (GB)

( * ) Notice: Subject to any disclaimer, the term of this patent is extended or adjusted under 35 U.S.C. 154(b) by 254 days.

(21) Appl. No.: 10/561,051

(22) PCT Filed: Jun. 18, 2004

(86) PCT No.: PCT/GB2004/002680

§ 371 (c)(1),
(2), (4) Date: Jun. 8, 2006

(87) PCT Pub. No.: WO2004/113349

PCT Pub. Date: Dec. 29, 2004

(65) Prior Publication Data

US 2007/0191608 A1   Aug. 16, 2007

(30) Foreign Application Priority Data

Jun. 20, 2003 (GB) ................... 0314493.8
Dec. 19, 2003 (GB) ................... 0329471.7

(51) Int. Cl.
| | |
|---|---|
| *C07D 471/02* | (2006.01) |
| *C07D 491/02* | (2006.01) |
| *C07D 498/02* | (2006.01) |
| *C07D 513/02* | (2006.01) |
| *C07D 515/02* | (2006.01) |

(52) U.S. Cl. .................................... 546/114
(58) Field of Classification Search ............... 546/114, 546/116
See application file for complete search history.

(56) References Cited

U.S. PATENT DOCUMENTS 2,788,202 A   4/1957   Barrett ..................... 262/26

FOREIGN PATENT DOCUMENTS

| WO | WO 04/000846 A1 | 12/2003 |
|---|---|---|
| WO | WO 2004/014920 A1 | 2/2004 |

OTHER PUBLICATIONS

Erian et al., Heterocycles, vol. 41, 1995, pp. 2195-2202.*
Adhikari, et al., "An adventitious synthesis of 2,2'-dipyrryl disulfides," *Aust. J. Chem.*, 1999, 52, 63-67.
Hartwig, J.F., "Transition metal catalyzed synthesis of arylamines and aryl ethers from aryl halides and triflates: scope and mechanism," *Angew. Chem., Int. Ed. Engl.*, 1998, 37, 2046-2067.
Hedayatullah, M., "Alkylation des pyrimidines en catalyse par transfert de phase," *J. Heterocyclic Chem.*, 1981, 18, 339 (no English abstract).
Luker, T.J., et al., "Palladium catalysed amination of electron deficient halothiophenes," *Tetrahedron Lett.*, 2001, 41, 7731-7735.
Nicolaides, E.D., et al., "Modified Di- and tripeptides of the C-Terminal portion of oxytocin and vasopressin as possible cognition activation agents," *J. Med. Chem.*, 1986, 29, 959-971.
Wolfe, J.P., "Scope and limitations of the Pd/BINAP-catalyzed amination of aryl bromides," *J. Org. Chem.*, 2000, 65, 1144-1157.

* cited by examiner

*Primary Examiner*—D. Margaret Seaman
*Assistant Examiner*—Niloofar Rahmani
(74) *Attorney, Agent, or Firm*—McDonnell Boehnen Hulbert & Berghoff LLP

(57) ABSTRACT

This invention provides a class of 3-amino-7H-thieno[2,3-b]pyridin-6-one derivatives, substituted in the 7-position by an aryl, heteroaryl, cycloalkyl or heterocycloalkyl moiety, and in the 2-position by a specified range of substituent groups; also provided is a process for preparing those compounds, and the use thereof as intermediates in the manufacture of certain p38 MAP kinase inhibitors.

21 Claims, No Drawings

PROCESS FOR PREPARING 3-AMINOTHIENOPYRIDONE DERIVATIVES

The present invention relates to 3-aminothienopyridone derivatives, to processes for their preparation and to their use as intermediates in the manufacture of inhibitors of p38 kinase (also known as p38 MAP kinase).

In co-pending PCT application number PCT/GB03/02667 (based on UK patent application GB 0214268.5), published as WO 2004/000846 on 31 Dec. 2003, we describe a series of bicyclic heterocycle derivatives of formula (A):

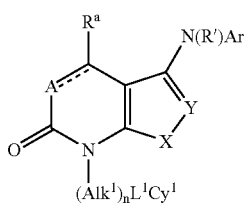

(A)

The compounds are potent and selective inhibitors of p38 kinases and are of use in the treatment of autoimmune, inflammatory and other diseases.

In co-pending PCT application number PCT/GB03/02667 the compounds of formula (A) are generally prepared by reaction of a bromide of formula (B):

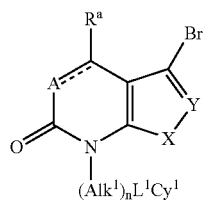

(B)

with an amine $ArNH_2$, in the presence of a palladium catalyst, a phosphine ligand and a base.

The bromide (B) is generally prepared in a multi-step process from a cyanopyridine or cyanopyrimidine of formula (C):

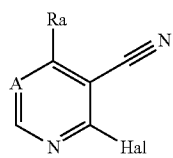

(C)

For example, compounds of formula (B) wherein A is a —C($R^b$)═ group, X is a —O— or —S— atom or —NH— group, and Y is a substituted carbon atom in which the substituent is an esterified carboxyl group, for example a —$CO_2Alk^2$ group, may be prepared in several steps, starting by reacting a compound of formula (C) with a reagent of formula $HXCH_2CO_2Et$ (where Et is an ethyl group and X is a —O— or —S— atom or —NH— group) to give an amine of formula (D):

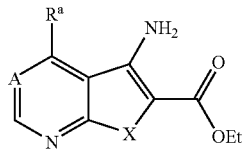

(D)

The resulting amine of formula (D) may be converted to a bromide by reaction with an alkyl nitrite and a copper salt, e.g. copper(II) bromide. The resulting bromide may then be oxidised to give a pyridine-N-oxide, which then undergoes rearrangement to give a pyridone, which is then finally N-alkylated or N-arylated to yield a desired bromide of formula (B).

Although the process to the bromides of formula (B) in PCT application number PCT/GB03/02667 is suitable for preparing compounds of formula (A) in acceptable yields, we have now found an improved process for preparing certain halides, such as bromides, comprising the use of an intermediate of formula (2). Thus in one aspect of the invention we provide a compound of formula (2):

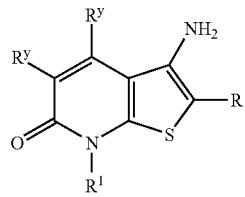

(2)

wherein

R is a —CN, —$NO_2$, —$CO_2Alk^2$, —$COC_{1-6}$alkyl or —$CONHet^2$ group;

$Alk^2$ is an optionally substituted alkyl, arylalkyl-, aryl, aryloxyalkyl-, alkanoyloxyalkyl- or aroyloxyalkyl- group;

$NHet^2$ is an optionally substituted 4- to 6-membered heterocycloalkyl group attached through a nitrogen atom to the group —CO;

$R^1$ is an optionally substituted aryl, heteroaryl, cycloalkyl or heterocycloalkyl group; and $R^y$, which may be the same or different, is each a hydrogen atom or a hydrogen atom precursor; and the salts, solvates, hydrates, protected derivatives and N-oxides thereof; for use in the manufacture of halides of formula (1), as defined below.

The intermediate amines of formula (2) are novel compounds and form a further aspect of the invention.

The amines of formula (2) are versatile and useful compounds. In particular they are of use in the preparation of halides, e.g. bromides, of formula (1) or amines of formula (1A) as described below. The processes are simple, versatile, short and easy to operate and are particularly amenable to the large-scale synthesis of the desired compounds.

Thus according to another aspect of the invention we provide a process for the manufacture of a halide of formula (1):

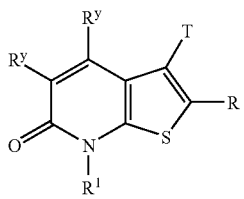

(1)

wherein R, $R^1$ and $R^y$ are as defined for formula (2) and T is a halogen atom; which comprises diazotization of an intermediate amine of formula (2), followed by halide displacement.

The process according to this aspect of the invention may be performed in the presence of a diazotization reagent, e.g. a nitrite such as an alkyl nitrite, for example tert-butyl nitrite, or a metal nitrite such as an alkali metal nitrite, e.g. sodium nitrite, in the presence of an inorganic acid such as sulphuric acid or hydrochloric acid, followed by addition of a source of halide such as a copper salt, for example copper(II) bromide, copper(II) chloride or copper(II) iodide, in the presence of a solvent, for example a nitrile such as acetonitrile, at a temperature from about 0° to around 65° C.

In addition to their use in the process described above compounds of formula (2) may also be used for other purposes such as for the direct preparation of certain compounds of formula (1A). The invention extends to such other uses and in particular we provide a process for the preparation of compounds of formula (1A):

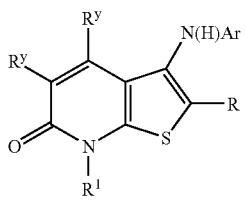

(1A)

wherein R, $R^1$ and $R^y$ are as defined for formula (2) and Ar is an optionally substituted aromatic or heteroaromatic group; which comprises reacting a compound of formula (2), as defined above, with a compound ArQ, wherein Q is a leaving group, in the presence of a transition metal catalyst, e.g. a palladium catalyst.

The reaction may be conveniently carried out in a solvent such as toluene or ethylene glycol dimethyl ether at an elevated temperature, e.g. the reflux temperature, using a catalyst such as tris(dibenzylideneacetone)-dipalladium(0), a phosphine ligand such as 2,2'-bis(diphenylphosphino)-1,1'-binaphthyl or tri-tert-butylphosphine, and a base such as caesium carbonate or tripotassium phosphate. Alternatively, the reaction may be carried out in the presence of a copper catalyst, e.g. copper(I) iodide, optionally in a suitable solvent such as an alcohol, e.g. isopropanol, or an ether, e.g. 1,4-dioxane, in the presence of a base, e.g. tripotassium phosphate. A chelating ligand such as ethylene glycol or N,N-dimethylethanolamine may also be used.

The novel intermediates of formula (2) may be prepared by a number of processes, as described hereinafter, and these form further aspects of the invention.

In the compounds of formulae (1), (1A) and (2) and where appropriate in the other formulae described herein the various terms used to define each substituent are to be understood to have the meanings as defined hereinafter, unless otherwise stated.

It will be appreciated that compounds of formulae (1), (1A) and (2) may have one or more chiral centres, and exist as enantiomers or diastereomers. The invention is to be understood to extend to all such enantiomers, diastereomers and mixtures thereof in any proportion, including racemates. Formulae (1), (1A) and (2) and the formulae hereinafter are intended to represent all individual isomers and mixtures thereof, unless stated or shown otherwise. In addition, compounds of formulae (1), (1A) and (2) may exist as tautomers, for example keto (CH2C=O)-enol (CH=CHOH) tautomers. Formulae (1), (1A) and (2) and the formulae hereinafter are intended to represent all individual tautomers and mixtures thereof, unless stated otherwise.

It will be further appreciated by one skilled in the art that the term "protected derivatives" is intended to mean that the relevant compound will include any group which may be readily removed from a compound of formulae (1), (1A) and (2). Conventional protecting groups may be used in accordance with standard practice (see, for example, Greene, T. W. in "Protective Groups in Organic Synthesis", John Wiley and Sons, 1999). Examples include amine protecting groups, such as carbamates, for example tert-butyl carbamate (BOC) or benzyl carbamate (Cbz), or alcohol protecting groups, for example esters such as methyl or ethyl ester, or benzyl ethers, for example, para-methoxybenzyl ether or benzyl ether, or ethers such as tetrahydropyran-2-yl ether, or alkyl ethers, e.g. methoxy.

It will also be appreciated that the term "hydrogen atom precursor" is intended to include any atoms or groups which may be readily removed from a compound of formulae (1), (1A) and (2), or any subsequent compound, in order to give a hydrogen atom. Suitable examples include halogen atoms, such as chlorine, bromine or iodine, or —$CO_2H$, esters, e.g. —$CO_2Alk^2$, or —CN groups.

Examples of leaving groups represented by the group Q include halogen atoms, e.g. a bromine, iodine or chlorine atom, or sulfonyloxy groups such as an alkylsulfonyloxy, e.g. trifluoromethylsulfonyloxy, or arylsulfonyloxy, e.g. p-toluenesulfonyloxy, groups. Particular examples include halogen atoms, especially bromine or iodine.

Thus as used herein the term "alkyl", whether present as a group or part of a group, includes straight or branched $C_{1-6}$ alkyl groups, for example $C_{1-4}$ alkyl groups such as methyl, ethyl, n-propyl, isopropyl, n-butyl, sec-butyl, isobutyl or tert-butyl groups. Optional substituents when present on these groups include those optional substituents mentioned hereinafter.

The term "alkylene chain" is intended to include the alkyl groups as just described in which a terminal hydrogen atom is replaced by a covalent bond to give a divalent chain. Examples include optionally substituted $C_{1-6}$ alkylene chains such as —$CH_2$—, —$CH_2CH_2$—, —$CH(CH_3)CH_2$—, —$(CH_2)_2CH_2$—, —$(CH_2)_3CH_2$—, —$CH(CH_3)(CH_2)_2$ $CH_2$—, —$CH_2CH(CH_3)CH_2$—, —$C(CH_3)_2$—, —$C(CH_3)_2$ $CH_2$—, —$CH_2C(CH_3)_2CH_2$—, —$(CH_2)_2CH(CH_3)CH_2$—, —$CH(CH_3)CH_2CH_2$—, —$CH(CH_3)CH_2CH(CH_3)CH_2$—, —$CH_2CH(CH_3)CH_2CH_2$—, —$(CH_2)_2C(CH_3)_2CH_2$—, —$(CH_2)_4CH_2$— or —$(CH_2)_5CH_2$—. Optional substituents when present on these chains include those optional substituents mentioned hereinafter.

The term halogen is intended to include fluorine, chlorine, bromine and iodine atoms.

The term "haloalkyl" is intended to include those alkyl groups just mentioned substituted by one, two or three of the halogen atoms just described. Particular examples of such groups include —$CF_3$, —$CCl_3$, —$CHF_2$, —$CHCl_2$, —$CH_2F$ and —$CH_2Cl$ groups.

The term "alkoxy" as used herein is intended to include straight or branched $C_{1-6}$ alkoxy, e.g. $C_{1-4}$ alkoxy such as methoxy, ethoxy, n-propoxy, isopropoxy, n-butoxy, sec-butoxy, isobutoxy and tert-butoxy. "Haloalkoxy" as used herein includes any of these alkoxy groups substituted by one, two or three halogen atoms as described above. Particular examples include —$OCF_3$, —$OCCl_3$, —$OCHF_2$, —$OCHCl_2$, —$OCH_2F$ and —$OCH_2Cl$ groups.

As used herein the term "alkylthio" is intended to include straight or branched $C_{1-6}$ alkylthio, e.g. $C_{1-4}$ alkylthio such as methylthio or ethylthio.

The optional substituents which may be present on alkyl groups or alkylene chains include one, two, three or more substituents where each substituent may be the same or different and is selected from halogen atoms, e.g. fluorine, chlorine, bromine or iodine atoms, or —OH, —$CO_2H$, —$CO_2R^4$ (where $R^4$ is an optionally substituted straight or branched $C_{1-6}$ alkyl group), e.g. —$CO_2CH_3$ or —$CO_2C(CH_3)_3$, —$CONHR^4$, e.g. —$CONHCH_3$, —$CON(R^4)_2$, e.g. —$CON(CH_3)_2$, —$COR^4$, e.g. —$COCH_3$, $C_{1-6}$ alkoxy, e.g. methoxy or ethoxy, halo$C_{1-6}$alkoxy, e.g. trifluoromethoxy or difluoromethoxy, thiol (—SH), —$S(O)R^4$, e.g. —$S(O)CH_3$, —$S(O)_2R^4$, e.g. —$S(O)_2CH_3$, $C_{1-6}$ alkylthio, e.g. methylthio or ethylthio, amino, —$NHR^4$, e.g. —$NHCH_3$, or —$N(R^4)_2$, e.g. —$N(CH_3)_2$, groups. Where two $R^4$ groups are present in any of the above substituents these may be the same or different.

In addition when two $R^4$ alkyl groups are present in any of the optional substituents just described these groups may be joined, together with the N atom to which they are attached, to form a heterocyclic ring. Such heterocyclic rings may be optionally interrupted by a further heteroatom or heteroatom-containing group selected from —O—, —S—, —$N(R^4)$—, —C(O)— and —C(S)— groups. Particular examples of such heterocyclic rings include piperidinyl, pyrazolidinyl, morpholinyl, thiomorpholinyl, pyrrolidinyl, imidazolidinyl and piperazinyl rings.

In general in the compounds of formulae (1), (1A) and (2) the term "cycloalkyl group" includes optionally substituted non-aromatic cyclic or multicyclic saturated $C_{3-10}$ ring systems, such as cyclopropyl, cyclobutyl, cyclopentyl, cyclohexyl, cycloheptyl or cyclooctyl. Particular examples include optionally substituted $C_{3-6}$ cycloalkyl ring systems such as cyclopropyl, cyclobutyl, cyclopentyl and cyclohexyl groups. Optional substituents present on these groups include those substituents mentioned hereinafter.

The term "heterocycloalkyl group" refers to an optionally substituted non-aromatic 3- to 10-membered saturated monocyclic or multicyclic hydrocarbon ring system containing one, two, three or four heteroatoms or heteroatom-containing linker groups $L^1$ as defined hereinafter. Particular examples include 3- to 6-membered monocyclic ring systems containing one or two heteroatoms. Optional substituents present on the heterocycloalkyl groups include those substituents mentioned hereinafter.

When $L^1$ is present in heterocycloalkyl groups as a linker atom or group it may be any divalent linking atom or group. Particular examples include —O— or —S— atoms, or —C(O)—, —C(O)O—, —OC(O)—, —C(S)—, —S(O)—, —$S(O)_2$—, —$N(R^5)$— (where $R^5$ is a hydrogen atom or a straight or branched alkyl group), —$N(R^5)O$—, —$N(R^5)N$—, —$CON(R^5)$—, —$OC(O)N(R^5)$—, —$CSN(R^5)$—, —$N(R^5)CO$—, —$N(R^5)C(O)O$—, —$N(R^5)CS$—, —$S(O)_2N(R^5)$—, —$N(R^5)S(O)_2$—, —$N(R^5)CON(R^5)$—, —$N(R^5)CSN(R^5)$— or —$N(R^5)SO_2N(R^5)$— groups. Where $L^1$ contains two $R^5$ groups these may be the same or different.

Particular examples of heterocycloalkyl groups include optionally substituted tetrahydrofuranyl, tetrahydropyranyl, tetrahydrothiophenyl, pyrrolidinyl, pyrrolidinone, oxazolidinyl, oxazolidinone, dioxolanyl, e.g. 1,3-dioxolanyl, imidazolidinyl, pyrazolidinyl, tetrahydropyrimidinyl, thiazolidinyl, piperidinyl, homopiperidinyl, piperidinone, 1,4-dioxanyl, morpholinyl, morpholinone, 1,4-dithianyl, thiomorpholinyl, piperazinyl, homopiperazinyl, dihydroisothiazolyl, dihydroisothiazole 1,1-dioxide, e.g. 2,3-dihydroisothiazole 1,1-dioxide, and tetrahydropyrazinyl groups.

The optional substituents which may be present on the cycloalkyl or heterocycloalkyl groups include one, two, three or more substituents selected from halogen atoms, or $C_{1-6}$ alkyl, e.g. methyl or ethyl, halo$C_{1-6}$alkyl, e.g. halomethyl or haloethyl such as difluoromethyl or trifluoromethyl, optionally substituted by hydroxyl, e.g. —$C(OH)(CF_3)_2$, $C_{1-6}$ alkoxy, e.g. methoxy or ethoxy, halo$C_{1-6}$alkoxy, e.g. halomethoxy or haloethoxy such as difluoromethoxy or trifluoromethoxy, thiol, $C_{1-6}$ alkylthiol, e.g. methylthiol or ethylthiol, carbonyl (=O), thiocarbonyl (=S), imino (=$NR^{4a}$) (where $R^{4a}$ is an —OH group or a $C_{1-6}$ alkyl group) or -$(Alk^3)_vR^6$ groups, in which $Alk^3$ is a straight or branched $C_{1-3}$ alkylene chain, v is zero or the integer 1, and $R^6$ is a $C_{3-8}$cycloalkyl, —OH, —SH, —$N(R^7)(R^8)$ (in which $R^7$ and R8 is each independently selected from a hydrogen atom or an optionally substituted alkyl or $C_{3-8}$cycloalkyl group), —$OR^7$, —$SR^7$, —CN, —NO2, —$CO_2R^7$, —$SOR^7$, —$SO_2R^7$, —$SO_3R^7$, —$OCO_2R^7$, —$C(O)R^7$, —$OC(O)R^7$, —$C(S)R^7$, —$C(O)N(R^7)(R^8)$, —$OC(O)N(R^7)(R^8)$, —$N(R^7)C(O)R^8$, —$C(S)N(R^7)(R^8)$, —$N(R^7)C(S)R^8$, —$SO_2N(R^7)(R^8)$, —$N(R^7)SO_2R^8$, —$N(R^7)C(O)N(R^8)(R^9)$ (where $R^9$ is as defined for $R^7$), —$N(R^7)C(S)N(R^8)(R^9)$ or —$N(R^7)SO_2N(R^8)(R^9)$ group, or an optionally substituted aromatic or heteroaromatic group.

Examples of —$NHet^2$ groups are defined hereinafter.

Particular examples of $Alk^3$ chains include —$CH_2$—, —$CH_2CH_2$—, —$CH_2CH_2CH_2$— and —$CH(CH_3)CH_2$— chains.

When $R^6$, $R^7$, R3 and/or $R^9$ is present as a $C_{3-8}$ cycloalkyl group it may be, for example, a cyclopropyl, cyclobutyl, cyclopentyl or cyclohexyl group. Optional substituents which may be present on such groups include, for example, one, two or three substituents, which may be the same or different, selected from halogen atoms, for example fluorine, chlorine, bromine or iodine atoms, or hydroxy or $C_{1-6}$ alkoxy, e.g. methoxy, ethoxy or isopropoxy, groups.

When the groups $R^7$ and $R^8$ or $R^8$ and $R^9$ are both alkyl groups these groups may be joined, together with the N atom to which they are attached, to form a heterocyclic ring. Such heterocyclic rings may be optionally interrupted by a further heteroatom or heteroatom-containing group selected from —O—, —S—, —$N(R^8)$—, —C(O)— and —C(S)— groups. Particular examples of such heterocyclic rings include piperidinyl, pyrazolidinyl, morpholinyl, thiomorpholinyl, pyrrolidinyl, imidazolidinyl and piperazinyl rings.

When $R^6$ is an optionally substituted aromatic or heteroaromatic group it may be any such group as described hereinafter.

The terms "aromatic group" and "aryl group" are intended to include, for example, optionally substituted monocyclic ring $C_{6-12}$ aromatic groups, such as phenyl, or bicyclic fused ring $C_{6-12}$ aromatic groups, such as 1- or 2-naphthyl groups.

The terms "heteroaromatic group" and "heteroaryl group" are intended to include, for example, optionally substituted $C_{1-9}$ heteroaromatic groups containing, for example, one, two, three or four heteroatoms selected from oxygen, sulfur and nitrogen atoms (or oxidised versions thereof). In general, the heteroaromatic groups may be, for example, monocyclic or bicyclic fused ring heteroaromatic groups. Monocyclic heteroaromatic groups include, for example, five- or six-membered heteroaromatic groups containing one, two, three or four heteroatoms selected from oxygen, sulfur and nitrogen atoms. Bicyclic heteroaromatic groups include, for example, eight- to thirteen-membered fused-ring heteroaromatic groups containing one, two or more heteroatoms selected from oxygen, sulphur and nitrogen atoms.

Each of these aromatic or heteroaromatic groups may be optionally substituted by one, two, three or more $R^{10}$ atoms or groups as defined below.

Particular examples of monocyclic ring heteroaromatic groups of this type include pyrrolyl, furyl, thienyl, imidazolyl, N—$C_{1-6}$alkylimidazolyl, oxazolyl, isoxazolyl, thiazolyl, isothiazolyl, pyrazolyl, triazolyl, oxadiazolyl, thiadiazolyl, pyridyl, pyrimidinyl, pyridazinyl, pyrazinyl, tetrazolyl and triazinyl.

Particular examples of bicyclic ring heteroaromatic groups of this type include benzofuryl, benzothienyl, benzotriazolyl, indolyl, indazolinyl, benzimidazolyl, imidazo[1,2-a]pyridyl, benzothiazolyl, benzoxazolyl, benzisoxazolyl, benzopyranyl, quinazolinyl, quinoxalinyl, naphthyridinyl, pyrido[3,4-b]pyridyl, pyrido[3,2-b]pyridyl, pyrido[4,3-b]pyridyl, quinolinyl, isoquinolinyl and phthalazinyl.

Optional substituents which may be present on aromatic or heteroaromatic groups include one, two, three or more substituents, each selected from an atom or group $R^{10}$ in which $R^{10}$ is $R^{10a}$ or -$L^2$Alk$^5$($R^{10a}$)$_r$, where $R^{10a}$ is a halogen atom, or an amino (—$NH_2$), substituted amino, nitro, cyano, hydroxyl (—OH), substituted hydroxyl, formyl, carboxyl (—$CO_2H$), esterified carboxyl, thiol (—SH), substituted thiol, —$COR^{11}$ [where $R^{11}$ is an -$L^6$Alk$^3$($R^{10a}$)$_r$, aryl or heteroaryl group], —$CSR^{11}$, —$SO_3H$, —$SOR^{11}$, —$SO_2R^{11}$, —$SO_3R^{11}$, —$SO_2NH_2$, —$SO_2NHR^{11}$, —$SO_2N(R^{11})_2$, —$CONH_2$, —$CSNH_2$, —$CONHR^{11}$, —$CSNHR^{11}$, —$CON(R^{11})_2$, —$CSN(R^{11})_2$, —$N(R^{12})SO_2R^{11}$ (where $R^{12}$ is a hydrogen atom or a straight or branched alkyl group), —$N(SO_2R^{11})_2$, —$N(R^{12})SO_2NH_2$, —$N(R^{12})SO_2NHR^{11}$, —$N(R^{12})SO_2N(R^{11})_2$, —$N(R^{12})COR^{11}$, —$N(R^{12})CONH_2$, —$N(R^{12})CONHR^{11}$, —$N(R^{12})CON(R^{11})_2$, —$N(R^{12})CSNH_2$, —$N(R^{12})CSNHR^{11}$, —$N(R^{12})CSN(R^{11})_2$, —$N(R^{12})CSR^{11}$, —$N(R^{12})C(O)OR^{11}$, —$SO_2NHet^1$ [where —$NHet^1$ is an optionally substituted $C_{3-7}$ cyclicamino group optionally containing one or more other —O— or —S— atoms or —$N(R^{12})$—, —C(O)— or —C(S)— groups], —$CONHet^1$, —$CSNHet^1$, —$N(R^{12})SO_2NHet^1$, —$N(R^{12})CONHet^1$, —$N(R^{12})CSNHet^1$, —$SO_2N(R^{12})Het$ [where -Het is an optionally substituted monocyclic $C_{3-7}$ carbocyclic group optionally containing one or more other —O— or —S— atoms or —$N(R^{12})$—, —C(O)—, —S(O)— or —$S(O)_2$— groups], -Het, —$CON(R^{12})Het$, —$CSN(R^{12})Het$, —$N(R^{12})CON(R^{12})Het$, —$N(R^{12})CSN(R^{12})Het$, —$N(R^{12})SO_2N(R^{12})Het$, aryl or heteroaryl groups; $L^2$ is a covalent bond or a linker atom or group as hereinbefore defined for $L^1$; Alk$^5$ is an optionally substituted straight or branched $C_{1-6}$ alkylene chain optionally interrupted by one, two or three —O— or —S— atoms or —$S(O)_e$— (where e is an integer 1 or 2) or —$N(R^{12})$—, e.g. —$N(CH_3)$—, groups; and r is zero or the integer 1, 2 or 3. It will be appreciated that when two $R^{11}$ or $R^{12}$ groups are present in one of the above substituents the $R^{11}$ and $R^{12}$ groups may be the same or different.

When in the group -$L^2$Alk$^5$($R^{10a}$)$_r$, r is an integer 1, 2 or 3, it is to be understood that the substituent or substituents $R^{10a}$ may be present on any suitable carbon atom in -Alk$^5$. Where more than one $R^{10a}$ substituent is present these may be the same or different and may be present on the same or different atom in -Alk$^5$. Clearly, when r is zero and no substituent $R^{10a}$ is present the alkylene chain represented by Alk$^5$ becomes an alkyl group.

When $R^{10a}$ is a substituted amino group it may be for example a group —$NHR^{11}$ (where $R^{11}$ is as defined above) or a group —$N(R^{11})_2$ wherein each $R^{11}$ group is the same or different.

When $R^{10a}$ is a halogen atom it may be, for example, a fluorine, chlorine, bromine or iodine atom.

When $R^{10a}$ is a substituted hydroxyl or substituted thiol group it may be, for example, a group —$OR^{11}$ or —$SR^{12}$ respectively.

The term "arylalkyl" refers to a straight or branched alkyl group, as defined herein, wherein a terminal hydrogen atom is replaced with an aryl group, as defined herein.

The term "aryloxyalkyl" is intended to refer to a straight or branched alkyl group, as defined herein, wherein a terminal hydrogen atom is replaced with an aryl-O— group, where the aryl group is as defined herein.

The term "alkanoyloxyalkyl" refers to a straight or branched alkyl group wherein a terminal hydrogen atom is replaced with an alkyl-C(O)O— group, where the alkyl group is as defined herein.

The term "aroyloxyalkyl" refers to a straight or branched alkyl group, as defined herein, wherein a terminal hydrogen atom is replaced with an aryl-C(O)O— group, where the aryl group is as defined herein.

Esterified carboxyl groups represented by the group $R^{10a}$ include groups of formula —$CO_2$Alk$^6$ wherein Alk$^6$ is a straight or branched, optionally substituted $C_{1-8}$ alkyl group such as a methyl, ethyl, n-propyl, isopropyl, n-butyl, isobutyl, sec-butyl or tert-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$ aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxy-methyl or 2-naphthyloxymethyl group; an optionally substituted $C_{1-8}$alkanoyloxy $C_{1-8}$alkyl group such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the Alk$^6$ group include $R^{10a}$ atoms and groups as described above.

When Alk$^5$ is present in or as a substituent it may be, for example, a —$CH_2$—, —$CH(CH_3)$—, —$C(CH_3)_2$—, —$CH_2CH_2$—, —$CH_2CH_2CH_2$—, —$CH(CH_3)CH_2$—, —$CH_2CH_2CH_2CH_2$—, —$CH_2CH(CH_3)CH_2$—, —$CH(CH_3)CH_2CH_2$— or —$C(CH_3)_2CH_2$— chain, optionally interrupted by one, two or three —O— or —S— atoms or —S(O)—, —$S(O)_2$— or —$N(R^{12})$—, e.g. —$N(CH_3)$—, groups. The alkylene chains represented by Alk$^5$ may be optionally substituted by one, two or three halogen atoms in addition to any $R^{10a}$ groups that may be present.

It will be appreciated that when —$NHet^1$ or -Het forms part of a substituent the heteroatoms or heteroatom-containing groups that may be present within the ring —$NHet^1$ or -Het take the place of carbon atoms within the parent carbocyclic ring.

Thus when —$NHet^1$ or -Het forms part of a substituent each may be, for example, an optionally substituted pyrrolidinyl, imidazolidinyl, pyrazolidinyl, piperazinyl, morpholinyl, thiomorpholinyl, piperidinyl or thiazolidinyl group. Additionally -Het may represent, for example, an optionally substituted cyclopentyl or cyclohexyl group. Optional substituents which may be present on —NHEt$^1$ include those substituents described above for heterocycloaliphatic groups.

Particularly useful atoms or groups represented by $R^{10}$ include fluorine, chlorine, bromine or iodine atoms, or $C_{1-6}$ alkyl, e.g. methyl, ethyl, n-propyl, isopropyl, n-butyl or tert-butyl, optionally substituted phenyl, pyridyl, pyrimidinyl, pyrrolyl, furyl, thiazolyl or thienyl, $C_{1-6}$ hydroxyalkyl, e.g. hydroxymethyl or hydroxyethyl, carboxy$C_{1-6}$alkyl, e.g. carboxyethyl, $C_{1-6}$ alkylthio, e.g. methylthio or ethylthio, carboxy$C_{1-6}$alkylthio, e.g. carboxy-methylthio, 2-carboxyethylthio or 3-carboxypropylthio, $C_{1-6}$ alkoxy, e.g. methoxy or ethoxy, hydroxy$C_{1-6}$alkoxy, e.g. 2-hydroxyethoxy, optionally substituted phenoxy, pyridyloxy, thiazolyoxy, phenylthio or pyridylthio, $C_{3-7}$ cycloalkyl, e.g. cyclobutyl or cyclopentyl, $C_{5-7}$ cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$ alkylamino, e.g. methylamino or ethylamino, halo$C_{1-6}$alkylamino, e.g. fluoro-$C_{1-6}$alkylamino, (amino)(halo)$C_{1-6}$alkyl, e.g. —CH(CF$_3$)NH$_2$ or —C(CF$_3$)$_2$NH$_2$, amino (—NH$_2$), amino$C_{1-6}$alkyl, e.g. aminomethyl, aminoethyl, —CH(CH$_3$)NH$_2$ or —C(CH$_3$)$_2$NH$_2$, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy or dimethylaminopropoxy, imido such as phthalimido or naphthalimido, e.g. 1,8-naphthalimido, nitro, cyano, hydroxyl (—OH), formyl [HC(O)—], carboxyl (—CO$_2$H), —CO$_2$Alk$^6$ (where Alk$^6$ is as defined above), $C_{1-6}$ alkanoyl e.g. acetyl, optionally substituted benzoyl, thiol (—SH), thio$C_{1-6}$alkyl, e.g. thiomethyl or thioethyl, sulphonyl (—SO$_3$H), $C_{1-6}$ alkylsulphonyl, e.g. methylsulphonyl, aminosulphonyl (—SO$_2$NH$_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—CONH$_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH)NH$_2$, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkylamino, optionally substituted phenylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or tert-butoxycarbonylamino, or optionally substituted benzyloxy, pyridylmethoxy, thiazolylmethoxy, benzyloxycarbonylamino, benzyloxycarbonylamino$C_{1-6}$alkyl, e.g. benzyloxycarbonylaminoethyl, benzothio, pyridylmethylthio or thiazolylmethylthio groups.

Where desired, two $R^{10}$ substituents may be linked together to form a cyclic group such as a cyclic ether, e.g. a $C_{1-6}$ alkylenedioxy group such as methylenedioxy or ethylenedioxy.

It will be appreciated that where two or more $R^{10}$ substituents are present, these need not necessarily be the same atoms and/or groups. In general, the substituent(s) may be present at any available ring position on the aromatic or heteroaromatic group.

The presence of certain substituents in the compounds of formulae (1), (1A) and (2) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulfonates, e.g. methanesulfonates, ethanesulfonates or isothionates, arylsulfonates, e.g. p-toluenesulfonates, besylates or napsylates, phosphates, sulfates, hydrogensulfates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In one particular group of compounds of formula (2), and in the processes hereinafter, $R^1$ is an optionally substituted phenyl, monocyclic heteroaryl or $C_{3-7}$ cycloalkyl group especially an optionally substituted phenyl, pyridyl, pyrimidinyl, pyridazinyl, pyrazinyl, thienyl, indolyl, cyclopropyl, cyclobutyl, cyclopentyl or cyclohexyl group. Especially preferred is when $R^1$ is an optionally substituted phenyl or cyclopropyl group.

Each of the preferred $R^1$ cycloalkyl groups may be unsubstituted. When substituents are present these may in particular include halogen atoms, especially fluorine, chlorine or bromine atoms, or $C_{1-6}$ alkyl groups, especially $C_{1-3}$ alkyl groups, most especially a methyl group, or halo$C_{1-6}$alkyl groups, especially a fluoro$C_{1-6}$alkyl group, most especially a —CF$_3$ group, or $C_{1-6}$ alkoxy groups, especially a methoxy, ethoxy, propoxy or isopropoxy group, or halo$C_{1-6}$alkoxy groups, especially a fluoro$C_{1-6}$alkoxy group, most especially a —OCF$_3$ group, or a cyano (—CN), esterified carboxyl, especially —CO$_2$CH$_3$ or —CO$_2$C(CH$_3$)$_3$, nitro (—NO$_2$), amino (—NH$_2$), substituted amino, especially —NHCH$_3$ or —N(CH$_3$)$_2$, —C(O)R$^6$, especially —C(O)CH$_3$, or —N(R$^6$)C(O)R$^7$, especially —NHCOCH$_3$, group.

Particularly preferred optional substituents which may be present on $R^1$ aromatic or heteroaromatic groups include one, two or three atoms or groups —$R^{10a}$ or -L$^6$Alk$^5$(R$^{10a}$)$_r$ as hereinbefore defined. Particularly useful optional substituents include halogen atoms, especially fluorine, chlorine or bromine atoms, or $C_{1-6}$ alkyl groups, especially $C_{1-3}$ alkyl groups, most especially a methyl group, or halo$C_{1-6}$alkyl groups, especially a fluoro$C_{1-6}$alkyl group, most especially a —$CF_3$ group, or $C_{1-6}$alkoxy groups, especially a methoxy, ethoxy, propoxy or isopropoxy group, or halo$C_{1-6}$alkoxy groups, especially a fluoro-$C_{1-6}$alkoxy group, most especially a —$OCF_3$ group, or a cyano (—CN), carboxyl (—$CO_2H$), esterified carboxyl (—$CO_2Alk^6$), especially —$CO_2CH_3$, —$CO_2CH_2CH_3$ or —$CO_2C(CH_3)_3$, nitro (—$NO_2$), amino (—$NH_2$), substituted amino, especially —$NHCH_3$ or —$N(CH_3)_2$, —$COR^{11}$, especially —$COCH_3$, or —$N(R^{12})COR^{11}$, especially —$NHCOCH_3$, group.

Further preferred optional substituents which may be present on $R^1$ aromatic or heteroaromatic groups include groups of formula -$L^6Alk^5(R^{10a})_r$ in which r is the integer 1 or 2; $L^6$ is a covalent bond or an —O— or —S— atom or a —$N(R^3)$—, especially —NH— or —$N(CH_3)$—, —C(O)—, —C(S)—, —C(O)O—, —OC(O)—, —$N(R^3)$CO—, especially —NHCO—, or —$CON(R^3)$—, especially —CONH—, group; $Alk^5$ is a $C_{1-6}$ alkylene chain, especially a —$CH_2$—, —$CH_2CH_2$—, —$CH_2CH_2CH_2$— or —$CH_2CH_2CH_2CH_2$— chain; and $R^{10a}$ is a hydroxyl or substituted hydroxyl group, especially a —$OCH_3$, —$OCH_2CH_3$ or —$OCH(CH_3)_2$ group, or a —$NH_2$ or substituted amino group, especially a —$N(CH_3)_2$ or —$N(CH_2CH_3)_2$ group, or a - Het group, especially an optionally substituted monocyclic $C_{3-7}$ carbocyclic group containing one, two or three —O—, —S—, —$N(R^{12})$—, especially —NH— or —$N(CH_3)$—, or —C(O)— groups within the ring structure as previously described, most especially an optionally substituted pyrrolidinyl, imidazolidinyl, piperidinyl, e.g. N-methylpiperidinyl, morpholinyl, thiomorpholinyl or piperazinyl group, or $R^{10a}$ is an optionally substituted heteroaromatic group, especially a five- or six-membered monocyclic heteroaromatic group containing one, two, three or four heteroatoms selected from oxygen, sulphur and nitrogen atoms, such as an optionally substituted pyrrolyl, furyl, thienyl, imidazolyl, triazolyl, pyridyl, pyrimidinyl, triazinyl, pyridazinyl or pyrazinyl group. Particularly preferred optional substituents on the -Het groups just described include hydroxyl (—OH) and carboxyl (—$CO_2H$) groups or those preferred optional substituents just described in relation to the group $R^1$, especially when $R^1$ is a cycloalkyl group.

In one particularly preferred group of compounds of formula (2) $R^1$ is an optionally substituted phenyl group, especially a phenyl group optionally substituted by one, two or three substituents where at least one, and preferably two, substituents are located ortho to the bond joining $R^1$ to the remainder of the compound of formula (2). Particularly preferred ortho substituents include halogen atoms, especially fluorine or chlorine atoms, or $C_{1-3}$ alkyl groups, especially methyl groups, or $C_{1-3}$ alkoxy groups, especially methoxy, or halo$C_{1-3}$alkyl groups, especially —$CF_3$, or halo$C_{1-3}$alkoxy groups, especially —$OCF_3$, or cyano (—CN) groups. In this class of compounds a second or third optional substituent when present in a position other than the ortho positions of the ring $R^1$ may be preferably an atom or group —$R^{10a}$ or -$L^6Alk^5(R^{10a})_r$ as herein generally and particularly described. In another preference, the $R^1$ phenyl group may have a substituent para to the bond joining $R^1$ to the remainder of the compound of formula (2). Particular para substituents include those particularly preferred ortho substituents just described. Where desired, the para substituent may be present with other ortho or meta substituents as just mentioned.

Typical examples of the group $R^1$ include phenyl, 3-methylphenyl, 4-methylphenyl, 2-chlorophenyl and cyclopropyl, especially phenyl.

In one particular group of compounds of formula (2), and in the processes hereinafter, each $R^y$ is preferably a hydrogen atom.

Particular examples of the group —$CO_2Alk^2$ include those groups as defined hereinbefore for —$CO_2Alk^6$. More especially, $Alk^2$ in compounds of formula (2), and in the processes hereinafter, is preferably a $C_{1-6}$ alkyl group.

Particular examples of the group R include —CN, —$NO_2$, —$CO_2C_{1-6}$alkyl, —$COC_{1-6}$alkyl and —$CONHet^2$ groups. R in compounds of formula (2), and in the processes hereinafter, is preferably a —CN, —$CO_2CH_3$, —$CO_2CH_2CH_3$, —$COCH_3$ or —$CONHet^2$ group.

Particular examples of the group —$NHet^2$ include optionally substituted pyrrolidinyl, imidazolidinyl, pyrazolidinyl, thiazolidinyl, piperidinyl, morpholinyl, thiomorpholinyl and piperazinyl groups. In one particular group of compounds, —$NHet^2$ is an optionally substituted pyrrolidinyl group. In another particular group of compounds, —$NHet^2$ is an optionally substituted piperazinyl group.

Particularly preferred —$NHet^2$ substituents include one, two, three or four groups, which may be the same or different, selected from —OH, —$(Alk^{3a})$OH (where $Alk^{3a}$ is a straight or branched $C_{1-4}$ alkylene chain), —$OR^{7a}$ (where $R^{7a}$ is a straight or branched $C_{1-6}$ alkyl group), —$(Alk^{3a})OR^{7a}$, —$NR^{7b}R^{8a}$ (where $R^{7b}$ and $R^{8a}$ may be the same or different and is each independently a hydrogen atom or a straight or branched $C_{1-6}$ alkyl group), —$(Alk^{3a})NR^{7b}R^{8a}$ or a straight or branched $C_{1-6}$ alkyl group, or protected derivatives thereof. Each substituent may be present on any ring carbon atom. In one particular class of compounds of formula (2) one or two substituents are present, in the latter instance on separate ring carbon atoms. More particular substituents on —$NHet^2$ include —OH, —$CH_2OH$, —$CH(CH_3)OH$ and —$C(CH_3)_2OH$ groups, and protected derivatives thereof, especially a —OH or —$CH_2OH$ group. Particular examples of suitable protecting groups include esters, such as methyl or ethyl esters, or benzyl ethers, for example para-methoxybenzyl ether or benzyl ether, or ethers such as tetrahydropyran-2-yl ether, or alkyl ethers, e.g. methoxy. Typically the hydroxy-protecting group is a $C_{1-6}$ alkyl group, especially methyl, a benzyl group, or a tetrahydropyran-2-yl group, especially a tetrahydropyran-2-yl group.

A further example of a substituent on —$NHet^2$ is $C_{1-6}$ alkyl, especially ethyl.

Typical examples of the group R include —CN, —$CO_2CH_2CH_3$ and —COpyrrolidin-1-yl. Further examples of R include —CO[3-(tetrahydropyran-2-yloxy)]pyrrolidin-1-yl and —CO[2-(hydroxymethyl)]pyrrolidin-1-yl. Another example of R is —$NO_2$. An additional example of R is 4-ethylpiperazin-1-yl. In a particular embodiment, R is —CN.

It will be appreciated that these particular preferences may also apply to the resulting halides of formula (1) and compounds of formula (1A).

Suitable values of Ar include phenyl, pyridyl, pyrimidinyl, pyridazinyl, pyrazinyl, thienyl or indolyl, any of which groups may be optionally substituted by one or more substituents as defined above. In a particular embodiment, Ar represents optionally substituted phenyl.

Examples of suitable optional substituents on Ar include halogen (especially fluoro) and $C_{1-6}$ alkyl (especially methyl).

In one embodiment, Ar is phenyl. In another embodiment, Ar is methylphenyl, especially 3-methylphenyl. In a further embodiment, Ar is (fluoro)(methyl)phenyl, especially 4-fluoro-3-methylphenyl.

The novel intermediates of formula (2) may be prepared by any number of processes. One particular process, described immediately below, involves the use of a uracil derivative of formula (2a) or a hydroxy acrylic acid derivative of formula (2b).

Thus, in another aspect of the invention we provide a process for the manufacture of a compound of formula (2) comprising the steps of:

a) reacting a compound of formula (2a) or (2b):

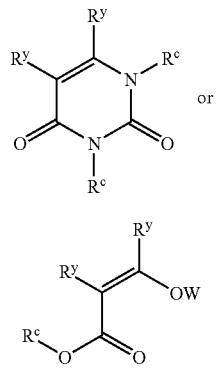

wherein $R^y$ is as defined herein, $R^c$ is an optionally substituted alkyl group, and W is a hydrogen atom, a metal ion or an amine salt; with a compound of formula (3):

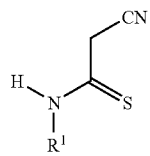

wherein $R^1$ is as defined herein;

b) followed by reaction with a compound of formula (5):

wherein R is as defined herein, and Z is a leaving group.

As used herein the term "leaving group" is intended to include any group which may be displaced during the course of a reaction. Examples include halogen atoms, e.g. a fluorine, chlorine, bromine or iodine atom, or sulfonyloxy groups such as alkylsulfonyloxy, e.g. trifluoromethylsulfonyloxy, or arylsulfonyloxy, e.g. p-toluenesulfonyloxy, groups. Particularly preferred Z groups include halogen atoms, especially chlorine or bromine.

Examples of the group W in compounds of formula (5) include H, metal ions such as Li, Na or K, and amine salts such as triethylamine, N,N-diisopropylethylamine or N-methylmorpholine. In one particular aspect of the process W is a metal ion, especially Na.

Particular examples of the group $R^c$ include $C_{1-3}$ alkyl groups, especially methyl.

Thus, in step a) of the process of the invention, a compound of formula (2a) or (2b) is reacted with a thioamide of formula (3). The reaction may be performed in the presence of a base. Appropriate bases may include, but are not limited to, lithium bases, such as n-butyllithium, tert-butyllithium or lithium diisopropylamide (LDA), or silazanes, e.g. lithium hexamethyldisilazane (LiHMDS) or sodium hexamethyldisilazane (NaHMDS), or carbonates, e.g. potassium carbonate, or alkoxides, e.g. sodium ethoxide, sodium methoxide or potassium tert-butoxide, or hydroxides, e.g. NaOH, or hydrides, e.g. sodium hydride, or organic amines, e.g. triethylamine or N,N-diisopropylethylamine, or cyclic amines, such as N-methylmorpholine or pyridine. The reaction may be performed in an organic solvent such as an amide, e.g. a substituted amide such as N,N-dimethylformamide, an ether, e.g. a cyclic ether such as tetrahydrofuran or 1,4-dioxane, an alcohol, e.g. methanol, ethanol or propanol, or acetonitrile, at a temperature from ambient to the reflux temperature. In one particular aspect of the process the reaction is achieved using an alkoxide base, especially sodium ethoxide or sodium methoxide in an alcoholic solvent, especially ethanol at the reflux temperature.

Intermediates of formula (2a), where not commercially available, may be prepared using standard methodology (see, for example, Mir Hedayatullah, *J. Heterocyclic Chem.*, 1981, 18, 339). Similarly, intermediates of formula (2b), where not commercially available, may be prepared using standard methodology. For example, they may be prepared in-situ by reaction of an ester, e.g. ethyl acetate, with a base such as sodium methoxide followed by addition of a formate, e.g. methyl formate.

In a similar manner, intermediates of formula (3), if not commercially available, may be prepared using methods known to those skilled in the art (see, for example Adhikari et al., *Aust. J. Chem.*, 1999, 52, 63-67). For example, an isothiocyanate of formula $R^1NCS$ may be reacted with acetonitrile in the presence of a base, e.g. NaHMDS, in a suitable solvent, e.g. tetrahydrofuran, optionally at a low temperature, e.g. around -78° C. According to the nature of the group $R^1$, the intermediate of formula (3) may be prepared in situ, for example using the methods as described herein, followed by subsequent addition of a compound of formulae (2a) or (2b).

During the course of this process an intermediate of formula (4) may be formed:

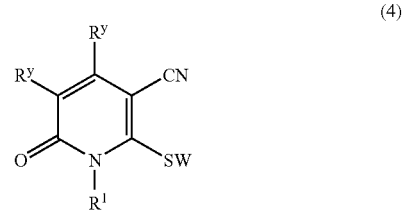

If desired the intermediate may be isolated at the end of step a) and subsequently reacted with intermediate (5) to form the desired amine. In some instances, however, it may advantageous not to isolate the intermediate of formula (4) and reaction b) may be carried out directly with the reaction mixture of step a).

If a different solvent is used during step b) of the process, it may be necessary to evaporate the solvent, in vacuo, from the first stage of the process before proceeding with the second stage. Once evaporated, the crude solids from step a) may be used in the next stage or they may be purified, for example by crystallisation, to yield an isolated intermediate, such as a compound of formula (4).

During step b) of the process an intermediate of formula (5) may then be added to the reaction mixture or to the crude solids or purified product from step a) in a suitable solvent. Suitable solvents include, but are not limited to, amides, e.g. a substituted amide such as N,N-dimethylformamide, alcohols, e.g. ethanol, methanol or isopropyl alcohol, ethers, e.g. a cyclic ether such as tetrahydrofuran or 1,4-dioxane, and acetonitrile. In one particular aspect of the process the reaction is carried out in acetonitrile. The reaction may be performed at a temperature from ambient up to the reflux temperature.

During the course of step b) an intermediate of formula (6):

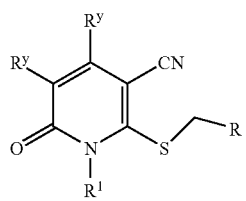

(6)

may be observed or even isolated, depending upon the nature of the group R. The intermediate of formula (6) may be converted into a compound of formula (1) using the methods described above. In this situation it may be necessary to add a base, in order for the reaction to proceed to completion. Appropriate bases include carbonates, e.g. caesium or potassium carbonate, or alkoxides, e.g. potassium tert-butoxide, or hydrides, e.g. sodium hydride, or organic amines, e.g. triethylamine or N,N-diisopropylethylamine, or cyclic amines, such as N-methylmorpholine or pyridine.

The intermediates of formulae (4) and (6) are novel and each form a further aspect of the invention.

It will be appreciated that intermediates of formula (5) where not commercially available may be prepared using standard methods known to those skilled in the art. For example, alcohol groups may be converted into leaving groups, such as halogen atoms or sulfonyloxy groups, using conditions known to the skilled artisan. For example, an alcohol may be reacted with thionyl chloride in a halogenated hydrocarbon, e.g. dichloromethane, to yield the corresponding chloride. A base, e.g. triethylamine, may also be used in the reaction.

It will be appreciated that intermediates, such as intermediates (2a), (2b), (3) or (5), if not available commercially, may also be prepared by methods known to those skilled in the art following procedures set forth in references such as Rodd's Chemistry of Carbon Compounds, Volumes 1-15 and Supplementals (Elsevier Science Publishers, 1989), Fieser and Fieser's Reagents for Organic Synthesis, Volumes 1-19 (John Wiley and Sons, 1999), Comprehensive Heterocyclic Chemistry, Ed. Katritzky et al, Volumes 1-8, 1984, and Volumes 1-11, 1994 (Pergamon), Comprehensive Organic Functional Group Transformations, Ed. Katritzky et al, Volumes 1-7, 1995 (Pergamon), Comprehensive Organic Synthesis, Ed. Trost and Fleming, Volumes 1-9 (Pergamon, 1991), Encyclopedia of Reagents for Organic Synthesis, Ed. Paquette, Volumes 1-8 (John Wiley and Sons, 1995), Larock's Comprehensive Organic Transformations (VCH Publishers Inc., 1989) and March's Advanced Organic Chemistry (John Wiley and Sons, 1992).

Where desired the process according to the invention may be extended by optionally employing one or more subsequent reactions to convert a compound of formula (2) into a further compound of formula (2), for example using methods as described hereinafter.

The process according to the invention is particularly useful for manufacturing certain halides of formula (1). These may then be converted into compounds of formula (1A), for example, as shown in Scheme 1 below:

Scheme 1

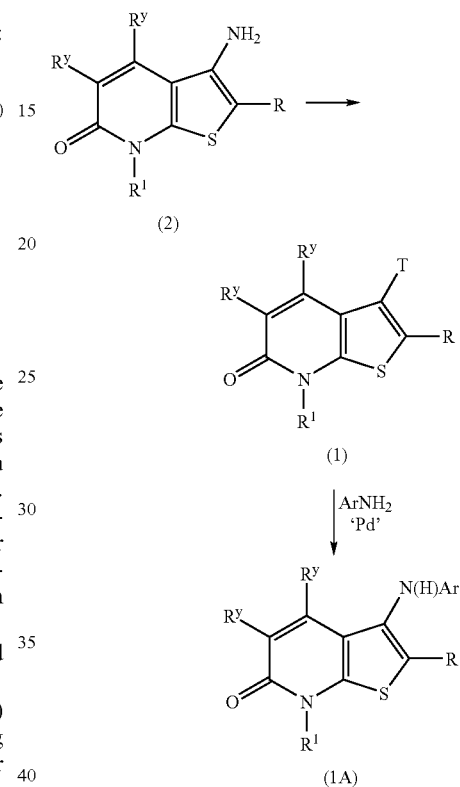

Thus in Scheme 1 a compound of formula (1A) may be prepared by reaction of a compound of formula (1) with an amine $ArNH_2$ in the presence of a transition metal catalyst, e.g. a palladium catalyst. The reaction may be conveniently carried out in a solvent such as toluene or ethylene glycol dimethyl ether at an elevated temperature, e.g. the reflux temperature, using a catalyst such as tris(dibenzylideneacetone)dipalladium(0), a phosphine ligand such as 2,2'-bis(diphenylphosphino)-1,1'-binaphthyl or tri-tert-butylphosphine and a base such as caesium carbonate or tripotassium phosphate. Where desired, alternative reaction conditions may be used, for example as described in the literature (Luker et al., *Tetrahedron Lett.*, 2001, 41, 7731; Buchwald, S. L., *J. Org. Chem.*, 2000, 65, 1144; Hartwig, J. F., *Angew. Chem., Int. Ed. Engl.*, 1998, 37, 2046).

Intermediates of formula (1) in Scheme 1 may be obtained by standard methods such as, for example, by the Sandmeyer reaction. Thus, for example, a halide of formula (1) may be prepared by treatment of a compound of formula (2) with a diazotization reagent, e.g. an alkyl nitrite, for example tert-butyl nitrite or sodium nitrite, in the presence of an acid, e.g. sulphuric acid or hydrochloric acid, followed by addition of a source of halide such as a copper salt, for example copper(II) bromide, copper(II) chloride or copper(II) iodide, in the presence of a solvent, for example a nitrite such as acetonitrile, at a temperature from about 0° to around 65° C. In one particular aspect of the process T is a bromine atom.

Alternatively, in a further aspect of the invention a compound of formula (1A) may be prepared according to the reaction set out in Scheme 2 below:

Scheme 2

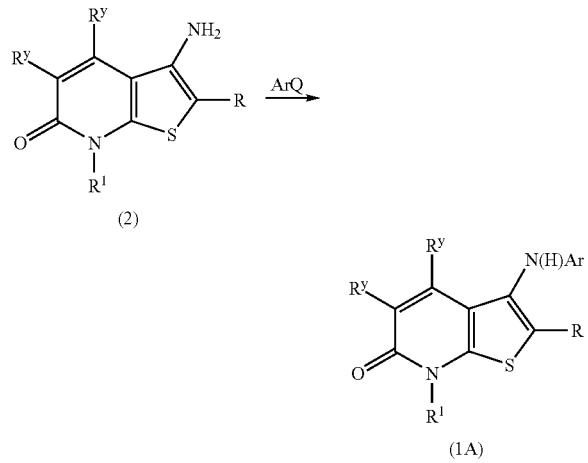

Thus in Scheme 2 a compound of formula (1A) may be prepared by reaction of a compound of formula (2) with a compound ArQ, wherein Q is a leaving group, in the presence of a transition metal catalyst e.g. a palladium catalyst. The reaction may be conveniently carried out in a solvent such as toluene or ethylene glycol dimethyl ether at an elevated temperature, e.g. the reflux temperature, using a catalyst such as tris(dibenzylideneacetone)dipalladium(0), a phosphine ligand such as 2,2'-bis(diphenylphosphino)-1,1'-binaphthyl or tri-tert-butylphospine and a base such as caesium carbonate or tripotassium phosphate. Where desired, alternative reaction conditions may be used, for example as described in the literature (Luker et al., *Tetrahedron Lett.*, 2001, 41, 7731; Buchwald, S. L., *J. Org. Chem.*, 2000, 65, 1144; Hartwig, J. F., *Angew. Chem., Int. Ed. Engl.*, 1998, 37, 2046). In one particular aspect of the process Q is a halogen atom, especially a bromine atom.

In an alternative embodiment a copper catalyst, e.g. copper (I) iodide, may be employed. The reaction may be performed in the presence of a base, e.g. tripotassium phosphate, optionally in a suitable solvent such as an alcohol, e.g. isopropanol, or an ether, e.g. 1,4-dioxane. A chelating ligand such as ethylene glycol or N,N-dimethylethanolamine may also be used. In reactions of this type Q is typically a halogen atom, especially an iodine atom.

It will be appreciated that the compounds of formulae (1) or (1A), such as those as formed in the process as defined herein, or any preceding intermediates may be further derivatised during the processes described above by one or more standard synthetic methods employing substitution, oxidation, reduction or cleavage reactions. Such reactions are optional additional process steps to those described above, and the invention is to be understood to extend to such optional steps. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other compounds of any of formula (1) or (1A) or any preceding intermediates where appropriate functional groups exist in these compounds.

Thus, for example, if the group $R^y$ is present this may be removed to give a hydrogen atom, using standard methods known to those skilled in the art. For example, decarboxylation using copper in the presence of quinoline may be employed to remove carboxylic acids. Halogen atoms may be removed, for example using Friedel—Crafts catalysts, such as $AlCl_3$, or by hydrogenation.

Ester groups such as $—CO_2Alk^2$ in the compounds of formulae (1) and (1A) and intermediates thereto may be converted into the corresponding acid ($—CO_2H$) by acid- or base-catalysed hydrolysis depending on the nature of the group $Alk^2$. Acid- or base-catalysed hydrolysis may be achieved, for example, by treatment with an organic or inorganic acid, e.g. trifluoroacetic acid, in an organic solvent, e.g. dichloromethane, or a mineral acid such as hydrochloric acid in a solvent such as 1,4-dioxane, or an alkali metal hydroxide, e.g. lithium hydroxide, in an aqueous alcohol, e.g. aqueous methanol.

Amides may be prepared from the corresponding acid, using standard methodology. For example, an acid chloride —COCl (prepared from the corresponding acid using methods known to those skilled in the art) may be reacted with a secondary amine in the presence of a base, such as a hydride, e.g. sodium hydride, or an amine, e.g. triethylamine or N-methylmorpholine, in a solvent such as a halogenated hydrocarbon, e.g. dichloromethane or carbon tetrachloride, or a dipolar aprotic solvent such as an amide, e.g. N,N-dimethylformamide, or an ether, e.g. a cyclic ether such as tetrahydrofuran, at for example ambient temperature. Alternatively, an acid may be reacted with a primary or secondary amine in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound, e.g. a N-hydroxytriazole such as 1-hydroxybenzotriazole. Alternatively an acid may be reacted with a chloroformate, for example ethyl chloroformate, prior to the desired reaction with a secondary amine.

Nitriles may be hydrolysed to give primary amides, for example using a base such as a hydroxide, e.g. sodium hydroxide, in for example water and an alcohol, e.g. ethanol.

Further interconversions are discussed in co-pending PCT application number PCT/GB03/02667.

N-Oxides may be prepared, for example, by oxidation of the corresponding nitrogen base using an oxidising agent such as hydrogen peroxide in the presence of an acid such as acetic acid at an elevated temperature, for example around 70° C. to 80° C., or alternatively by reaction with a peracid such as peracetic acid in a solvent, e.g. dichloromethane, at ambient temperature.

Salts may be prepared by reaction with an appropriate base in a suitable solvent or mixture of solvents, e.g. an organic solvent such as an ether, e.g. diethyl ether, or an alcohol, e.g. ethanol, using conventional procedures.

Where it is desired to obtain a particular enantiomer this may be produced from a corresponding mixture of enantiomers using any suitable conventional procedure for resolving enantiomers.

Thus, for example, diastereomeric derivatives, e.g. salts, may be produced by reaction of a mixture of enantiomers, e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt.

In another resolution process a racemate may be separated using chiral High Performance Liquid Chromatography. Alternatively, if desired a particular enantiomer may be obtained by using an appropriate chiral intermediate in one of the processes of the invention described above. Alternatively, a particular enantiomer may be obtained by performing an enantiomer-specific enzymatic biotransformation, e.g. an ester hydrolysis using an esterase and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention.

The following Examples illustrate the present invention in more detail; however, they are not intended to limit its scope in any manner.

All temperatures are in ° C. The following abbreviations are used:
EtOAc—ethyl acetate;
MeOH—methanol;
EtOH—ethanol;
DMSO—dimethylsulphoxide;
$H_2O$—water;
NaHMDS—sodium bis(trimethylsilyl)amide;
$CDCl_3$—deuterated chloroform;
DME—ethylene glycol dimethyl ether;
BINAP—2,2'-bis(diphenylphosphino)-1,1'-binaphthyl;
$Pd_2(dba)_3$—tris(dibenzylideneacetone)dipalladium(0);
EDTA—ethylenediaminetetraacetic acid.
DCM—dichloromethane;
MeCN—acetonitrile;
$Et_2O$—diethyl ether;
THF—tetrahydrofuran;
r.t.—room temperature;
MIBK—4-methyl-2-pentanone;

All NMR's were obtained either at 300 MHz or 400 MHz. All Intermediates and Examples were named with the aid of Beilstein Autonom (available from MDL Information Systems GmbH, Therdor-Heuss-Allee 108D, 60486, Frankfurt, Germany) or were given names that seemed consistent.

LCMS retention times (RT) quoted were generated on a Hewlett Packard 1100/ThermoFinnigan LCQ Duo LC/MS system using Electrospray ionisation and the following LC method: Phenomenex Luna $C_{18}(2)$ 5 μ 100 mm×4.6 mm column; mobile phase A=0.08% formic acid in water; mobile phase B=0.08% formic acid in MeCN; flow rate of 3.0 mLmin$^{-1}$, column temperature 35° C.

Gradient:

| Time (min) | % A | % B |
|---|---|---|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Gas Chromatographs were run on a Perkin Elmer Autosystem instrument, using an SGE 25QC2 BP5 1.0 column. Initial temperature, 70° C., heat at 15° C./min to 250° C., hold 10 min. Injector temperature 150° C., detector temperature 250° C.

Intermediate 1

2-Cyano-N-phenylthioacetamide

The title compound was prepared according to Adhikari et al., *Australian J. Chem.*, 1999, 52, 63-67. δH (DMSO-d6) 11.95 (1H, br s), 7.80 (2H, d, J 7.4 Hz), 7.45 (2H, dd, J 7.4 Hz, 7.4 Hz), 7.30 (1H, t, J 7.4 Hz), 4.29 (2H, s).

Intermediate 2

2-Chloro-1-(pyrrolidin-1-yl)ethanone

The title compound was prepared according to U.S. Pat. No. 2,788,202. δH (CDCl$_3$) 4.04 (2H, s), 3.55 (4H, m), 2.10-1.85 (4H, m).

Intermediate 3

(R)-3-(Tetrahydropyran-2-yloxy)pyrrolidine

Methyl formate (23 ml) was added dropwise over 15 min to a cooled solution of (R)-pyrrolidin-3-ol (25 g) in MeOH (12 ml), maintaining the temperature at below 15° C. Once the addition was complete, the reaction was stirred for a further 30 min. GC analysis showed the reaction was complete. The excess MeOH and methyl formate were removed by concentration under vacuum on a rotary evaporator. Toluene (50 ml) was added and the mixture concentrated again to ensure complete removal. The (R)-3-hydroxypyrrolidine-1-carbaldehyde was obtained in a 96% yield (32.3 g), 99% pure by GC, RT 10.0 min. δH (CDCl$_3$) 8.20 and 8.25 (2H, 2×s), 4.45-4.60 (1H, m), 3.40-3.80 (4H, m), 1.90-2.10 (2H, m).

The (R)-3-hydroxypyrrolidine-1-carbaldehyde (31 g) was treated with dihydropyran (36.8 ml) and p-toluenesulphonic acid (1 g). The mixture was stirred at room temperature for approximately one hour, during which time the colour changed from yellow to dark purple. GC analysis showed the reaction was complete. The reaction was quenched by addition of saturated sodium bicarbonate solution (90 ml). The aqueous phase was extracted with DCM (3×90 ml). The combined organic phase was washed with saturated sodium chloride solution (90 ml), then dried over MgSO$_4$ and concentrated at below 30° C. The product, 3-(tetrahydropyran-2-yloxy)pyrrolidine-1-carbaldehyde, was obtained in 100% yield, 54.5 g. GC analysis showed two adjacent peaks, RT 14.45 and 14.83 min, 49.7 and 47.1% respectively. δH (CDCl$_3$) 8.22 and 8.27 (1H, 2×s), 4.60-4.75 (1H, m), 4.35-4.50 (1H, m), 3.80-3.95 (1H, m), 3.40-3.70 (5H, m), 1.40-2.20 (8H, m).

A solution of KOH (5 g) in water (50 ml) was added to 3-(tetrahydropyran-2-yloxy)pyrrolidine-1-carbaldehyde. The mixture was heated at 50° C. for approximately one hour, after which time GC analysis showed the reaction was complete. After cooling to room temperature, the product was extracted with DCM (3×50 ml). The organic phase was dried over MgSO$_4$ and concentrated. The title compound was obtained in 100% yield, (8.5 g). GC analysis, RT 10.4 min, 96.6% purity. δH (CDCl$_3$) 4.60-4.70 (1H, m), 4.35-4.45 (1H, m), 3.80-3.95 (1H, m), 3.40-3.60 (1H, m), 2.90-3.25 (4H, m), 1.40-2.05 (8H, m).

Intermediate 4

2-Chloro-1-[(R)-3-(tetrahydropyran-2-yloxy)pyrrolidin-1-yl]ethanone

Intermediate 3 (2 g) was dissolved in DCM (30 ml) and cooled using an ice/water bath. Diisopropylethylamine (2.3 ml) was added. Chloroacetyl chloride (0.93 ml) was added dropwise over 1 hour, maintaining the temperature below 7° C. When the addition was complete, NaHCO$_3$ (30 ml, 5% w/v) was added. The mixture was stirred and allowed to warm to room temperature for one hour. The phases were separated, the organic phase was dried over MgSO$_4$ and concentrated. The title compound was obtained in a 93% yield (2.6 g) as a brown oil. δH (CDCl$_3$) 4.60-4.75 (1H, m), 4.40-4.55 (1H, m), 3.95-4.15 (2H, m), 3.45-3.95 (6H, m), 1.45-2.30 (8H, m). LCMS (ES$^+$) RT 2.54 min, 248 (M+H)$^+$.

Intermediate 5

2-Choro-1-((S)-2-hydroxymethylpyrrolidin-1-yl) ethanone

The title compound was prepared according to the method described in Nicolaides et al., *J. Med. Chem.*, 1986, 29, 959-971.

Intermediate 6

2-Chloro-1-(4-ethylpiperazin-1-yl)ethanone

Chloroacetyl chloride (6.63 ml) and triethylamine (13.4 ml) in DCM (20 ml) was added dropwise to 1-ethylpiperazine (10 g) in DCM (60 ml) under nitrogen. The mixture was stirred at room temperature for 17 hours then partitioned between DCM and H$_2$O (100 ml). The aqueous layer was neutralised using 1M NaOH before extracting into DCM. Organic layer dried (MgSO$_4$) and concentrated in vacuo. Purification by column chromatography (silica, 0 to 5% MeOH in DCM) gave the title compound as a pale oil (3.23 g, 19%). δH (CDCl$_3$) 4.08 (2H, s), 3.65 (2H, m), 3.55 (2H, m), 2.52-2.40 (6H, m), 1.10 (3H, t, J 7.2 Hz).

EXAMPLE 1

Sodium 3-cyano-6-oxo-1-phenyl-1,6-dihydropyridine-2-thiolate

Method A

A solution of sodium methoxide in MeOH (30 wt %, 202.2 g) was added to absolute EtOH (360 mL) followed by 1,3-dimethyluracil (75 g) and 2-cyano-N-phenylthioacetamide (90 g). The resulting mixture was heated at reflux for 8 h and then allowed to cool to ambient temperature overnight. The reaction mixture was then cooled to +5° C. and maintained at this temperature for at least an hour when the product was recovered by filtration. The filter cake was washed with cold (+5° C.) absolute EtOH (450 ml) and then dried to constant weight under vacuum at 45° C. to give the title compound as a pale pink solid (130.0 g). The product thus obtained contained residual EtOH and MeOH, estimated at 12.2 wt % by 1H NMR, corresponding to a corrected yield of 114.1 g. δH (DMSO-d6) 7.32 (2H, m), 7.27-7.18 (1H, m), 7.16 (1H, d, J 9.1 Hz), 6.92 (2H, m), 5.63 (1H, d, J 9.1 Hz). LCMS (ES$^+$) RT 2.43 minutes, 229 (M+H)$^+$.

Method B

Sodium methoxide (2.88 g) was added to EtOAc (8.7 mL), cooled to +14° C. To the resulting suspension was added methyl formate (2.2 mL) slowly over 4.3 h whilst maintaining the reaction temperature at +14° C. After this time, the temperature was adjusted to +25° C. and the reaction was allowed to stir out at this temperature overnight. Absolute EtOH (25 mL) and a solution of sodium methoxide in MeOH (30 wt %, 6.7 mL) were then added followed by 2-cyano-N-phenylth-ioacetamide (5 g) and the resulting mixture was heated at reflux for 24 h. The reaction was cooled to +5° C. when the product was recovered by filtration. The filter cake was washed with cold (+5° C.) absolute EtOH (20 ml) and then dried to constant weight under vacuum at 45° C. to give the title compound as a pale pink solid (2.77 g; equivalent to 2.63 g at 100%). δH (DMSO-d6) 7.32 (2H, m), 7.27-7.18 (1H, m), 7.16 (1H, d, J 9.1 Hz), 6.92 (2H, m), 5.63 (1H, d, J 9.1 Hz). LCMS (ES$^+$) RT 2.43 minutes, 229 (M+H)$^+$.

EXAMPLE 2

Sodium 1-(2-chlorophenyl)-3-cyano-6-oxo-1,6-dihydropyridine-2-thiolate

NaHMDS (13.2 mL, 1.0M in THF, 13.2 mmol) was added slowly to a solution of 2-chlorophenyl isothiocyanate (1.02 g, 6.0 mmol) in THF (50 mL) and acetonitrile (5 mL) at −78° C. The mixture was warmed to r.t. over 1 h. N,N-Dimethyluracil (841 mg, 6.0 mmol) and EtOH (75 mL) were added and the mixture heated at reflux for 4 h. Volatiles were removed in vacuo and the residue was dissolved in hot EtOH (10 mL). Et$_2$O (~100 mL) was added slowly to precipitate out the product. The solid was filtered off, washed with Et$_2$O (2×30 mL) and dried to give the title compound (1.5 g, 88%) (v. hygroscopic). δH (DMSO-d6) 7.35-7.32 (1H, m), 7.25-7.20 (2H, m), 7.15 (1H, d, J 9.1 Hz), 7.05-7.01 (1H, m), 5.85 (1H, br s), 5.58 (1H, d, J 9.1 Hz). LCMS (ES$^+$) RT 3.06 minutes, 285 (M+H)$^+$.

EXAMPLE 3

3-Amino-6-oxo-7-phenyl-6,7-dihydrothieno[2,3-b] pyridine-2-carbonitrile

A mixture of Example 1 (100 g at 100%) and chloroacetonitrile (30.4 mL) in MeCN (500 mL) was heated at reflux for 2 h. The mixture was cooled, initially to 40° C. when water (300 mL) was added, and then to +10° C. The reaction was maintained at +10° C. for at least 1 h when the product was recovered by filtration. The filter cake was washed with cold (+10° C.) H$_2$O (500 mL) followed by a cold (+10° C.) mixture of MeCN and H$_2$O (1:1, 300 mL). The product was dried under vacuum at 50° C. to constant weight to give the title compound as an off-white solid (100.9 g). δH (DMSO-d6) 7.90 (1H, d, J 9.6 Hz), 7.46-7.33 (3H, m), 7.25 (2H, m), 6.95 (2H, br s), 6.35 (1H, d, J 9.6 Hz). LCMS (ES$^+$) RT 2.69 minutes, 268 (M+H)$^+$.

EXAMPLE 4

3-Amino-6-oxo-7-phenyl-6,7-dihydrothieno[2,3-b] pyridine-2-carboxylic acid ethyl ester A mixture of Example 1 (0.34 g at 100%) and ethyl bromoacetate (0.197 mL) in EtOH (6 mL) was stirred at room temperature for 1 h. H$_2$O (10 mL) was then added. The solid was filtered and washed with more H$_2$O (2 mL). The product was dried under vacuum at 40° C. to constant weight to give the title compound as a pale pink solid (0.35 g). δH (DMSO-d6) 8.20 (1H, d, J 9.6 Hz), 7.60 (3H, m), 7.45 (2H, m), 7.15 (2H, br s), 6.55 (1H, d, J 9.6 Hz), 4.15 (2H, q, J 7.1 Hz), 1.20 (3H, t, J 7.1 Hz). LCMS (ES$^+$) RT 3.29 minutes, 315 (M+H)$^+$.

EXAMPLE 5

3-Amino-7-(2-chlorophenyl)-6-oxo-6,7-dihydrothieno[2,3-b]pyridine-2-carbonitrile Method A Chloroacetonitrile (0.35 mL, 5.5 mmol) was added to a solution of Example 2 (1.42 g, 5.0 mmol) in MeCN (50 mL) and the mixture heated at 40° C. for 3 h. $H_2O$ (100 mL) was added and the mixture concentrated in vacuo to remove some of the MeCN (remaining volume ~120 mL). The mixture was cooled to 0° C. and the solid filtered off, washed with $H_2O$ (15 mL) and $Et_2O$ (2×15 mL) and dried to give the title compound as a pale brown solid (505 mg, 32%). δH (DMSO-d6) 8.10 (1H, d, J 9.7 Hz), 7.75-7.73 (1H, m), 7.65-7.54 (3H, m), 7.14 (2H, br s, $NH_2$), 6.54 (1H, d, J 9.7 Hz). LCMS ($ES^+$) RT 2.97 minutes, 302 $(M+H)^+$.

Method B

MeCN (10 mL) was added to a solution of NaHMDS (100 mL, 1.0M in THF, 100 mmol) in THF (50 mL) at −78° C. to give a thick white precipitate. 2-Chlorophenyl isothiocyanate (7.72 g, 45.45 mmol) was added to give a brown solution. The mixture was allowed to warm to r.t. over 1 h then diluted with EtOH (50 mL). N,N-Dimethyluracil (6.4 g, 45 mmol) was added and the mixture heated at reflux for 24 h. Volatiles were removed in vacuo and the residue dissolved in MeCN (100 mL). Chloroacetonitrile (2.85 mL, 45 mmol) was added and the mixture heated at 50° C. for 1 h, a second charge of chloroacetonitrile (2.85 mL, 45 mmol) was added and heating continued for 1.5 h. Some of the MeCN (~50 mL) was removed in vacuo and $H_2O$ was added to precipitate the product. The brown solid was filtered off, washed with $H_2O$ (50 mL) and $Et_2O$ (50 mL) and dried to give the title compound as a brown solid (14.3 g, quant.). δH (DMSO-d6) 8.10 (1H, d, J 9.7 Hz), 7.75-7.73 (1H, m), 7.65-7.54 (3H, m), 7.14 (2H, br s, $NH_2$), 6.54 (1H, d, J 9.7 Hz). LCMS (ES+) RT 2.97 minutes, 302 (M+H)+.

EXAMPLE 6

Sodium 3-cyano-1-(2-methylphenyl)-6-oxo-1,6-dihydropyridine-2-thiolate

A solution of NaHMDS (84 mL of a 1.0M solution in THF, 84 mmol) was added to a solution of o-tolyl isothiocyanate (5.0 g, 33.5 mmol) and MeCN (18 mL) in THF (100 mL) at −78° C. The mixture was allowed to warm to r.t. over 3h. N,N-Dimethyluracil (4.62 g, 33 mmol) and EtOH (75 mL) were added and the mixture heated at reflux for 3 h then stirred at r.t. overnight. Volatiles were removed in vacuo. The residue was used crude in the next step without further purification.

EXAMPLE 7

3-Amino-7-(2-methylphenyl)-6-oxo-6,7-dihydrothieno[2,3-b]pyridine-2-carbonitrile A mixture of crude Example 6 (half of material obtained above) and chloroacetonitrile (1.94 mL) in MeCN (25 mL) was heated at reflux for 5 h. Volatiles were removed in vacuo. The residue was treated with $H_2O$ to give a solid which was filtered off and dried to give the title compound (3.0 g). δH (DMSO-d6) 8.16 (1H, d, J 9.6 Hz), 7.70-7.50 (4H, m), 7.19 (2H, s), 6.60 (1H, d, J 9.6 Hz), 2.00 (3H, s). LCMS ($ES^+$) RT 2.932 minutes, 281.9 $(M+H)^+$.

EXAMPLE 8

Sodium 3-cyano-1-(4-methylphenyl)-6-oxo-1,6-dihydropyridine-2-thiolate

NaHMDS (36.8 mL, 1.0M in THF, 36.8 mmol) was added slowly to a solution of 4-tolyl isothiocyanate (2.5 g, 16.75 mmol) in THF (30 mL) and MeCN (5 mL) at −78° C. The mixture was warmed to r.t. over 1 h. N,N-Dimethyluracil (2.35 g, 16.75 mmol) and EtOH (20 mL) were added and the mixture heated at reflux for 4 h. Volatiles were removed in vacuo and the residue was dissolved in EtOH (6 mL). $Et_2O$ (~60 mL) was added slowly to produce a fine, off-white solid. The suspension was cooled to 0° C. and the solid filtered off, washed with $Et_2O$ and dried to give the title compound as an off-white solid (1.7 g, 39%). δH (DMSO-d6) 7.15-7.12 (3H, m), 6.80-6.77 (2H, m), 5.60 (1H, d, J 9.1 Hz), 2.30 (3H, s).

EXAMPLE 9

3-Amino-7-(4-methylphenyl)-6-oxo-6,7-dihydrothieno[2,3-b]pyridine-2-carbonitrile Chloroacetonitrile (0.41 mL, 6.4 mmol) was added to a suspension of Example 8 (1.7 g, 6.44 mmol) in MeCN (40 mL). The mixture was heated at 45° C. for 2 h. Solvent was removed in vacuo and the residual solid was suspended in $H_2O$ (30 mL). The solid was filtered off, washed with $H_2O$ (3×10 mL) and $Et_2O$ (5 mL) and dried to give the title compound as an off-white solid (1.22 g, 67%). δH (DMSO-d6) 8.01 (1H, d, J 9.7 Hz), 7.34-7.32 (2H, m), 7.27-7.25 (2H, m), 7.00 (2H, br s), 6.45 (1H, d, J 9.7 Hz), 2.34 (3H, s). LCMS ($ES^+$) RT 3.03 minutes, 282.0 $(M+H)^+$.

EXAMPLE 10

3-Bromo-6-oxo-7-phenyl-6,7-dihydrothieno[2,3-b]pyridine-2-carbonitrile

To a mixture of anhydrous copper(II) bromide (23.4 g) and tert-butyl nitrite (14.8 mL) in MeCN (600 mL) at room temperature was added Example 3 (20 g) portionwise, at such a rate as to keep the internal temperature below 25° C. The addition took approximately 1 hour. Analysis by HPLC indicated almost complete conversion of starting material after a further 30 minutes of stirring. The reaction mixture was then poured onto 500 mL of 1 M HCl (caution: brown fumes given off). This was then extracted with DCM (2×400 mL). The combined organic extracts were then washed with 1 M HCl (3×300 mL), dried over $MgSO_4$ and evaporated to dryness. The resulting crude product was then recrystallised from MIBK (700 mL). The product was dried under vacuum at 50° C. to constant weight to give the title compound as a light brown solid (15.14 g). δH ($CDCl_3$) 7.75 (1H, d, J 8.5 Hz), 7.55-7.70 (3H, m), 7.35 (2H, m), 6.80 (1H, d, J 8.5 Hz). LCMS ($ES^+$) RT 3.54 minutes, no parent ion observed.

EXAMPLE 11

6-Oxo-7-phenyl-3-phenylamino-6,7-dihydrothieno[2,3-b]pyridine-2-carbonitrile Method A To a dry 100 ml 3-necked round-bottomed flask, fitted with nitrogen inlet/outlet, was added $K_3PO_4$ (5.90 g), $tBu_3PH.BF_4$ (110 mg), Example 3 (5.0 g) and $Pd_2(dba)_3$ (85.5 mg). To this mixture was added 50 ml of anhydrous DME, which had been thoroughly degassed. The reaction mixture was then put through a vacuum and nitrogen cycle. To the reaction mixture was added bromobenzene (3.25 g) via syringe. The reaction was then set to reflux. After 5 hours at reflux the reaction had gone to completion. The reaction mixture was cooled to ambient, and held at this temperature for 1 hour. The solid was then collected by filtration. This crude solid was then slurried in 50 ml of 1.0N HCl for 1 hour. The beige-coloured solid was collected by filtration, washing with $H_2O$ (50 ml). The product was then dried under vacuum at 50° C., to give the title compound as a light brown solid (5.27 g). δH (DMSO-d6) 9.60 (1H, s), 8.25 (1H, d, J 8.5 Hz), 7.75-7.90 (5H, m), 7.50 (2H, m), 7.40 (2H, m), 7.30 (1H, t, J 7.5 Hz), 6.85 (1H, d, J 8.5 Hz). LCMS (ES$^+$) RT 3.58 minutes, 344 (M+H)$^+$.

Method B

To a dry 50 ml 2-necked round-bottomed flask, fitted with nitrogen inlet/outlet, was added $Cs_2CO_3$ (1.38 g), (+/−)-BINAP (188 mg), Example 10 (1.00 g) and $Pd_2(dba)_3$ (138.4 mg). To this mixture was added 20 ml of anhydrous toluene, which had been thoroughly degassed. The reaction mixture was then put through a vacuum and nitrogen cycle. To the reaction mixture was added aniline (0.338 g) via syringe. The reaction was then set to reflux. After 16 hours at reflux the reaction had gone to completion. The reaction mixture was cooled to ambient, and held at this temperature for 1 hour. The solid was then collected by filtration. This crude solid was then slurried in 10 ml of 1.0N HCl for 1 hour. The beige-coloured solid was collected by filtration, washing with $H_2O$ (10 ml). The product was then dried under vacuum at 50° C., to give the title compound as a light brown solid (0.68 g). δH (DMSO-d6) 9.60 (1H, s), 8.25 (1H, d, J 8.5 Hz), 7.75-7.90 (5H, m), 7.50 (2H, m), 7.40 (2H, m), 7.30 (1H, t, J 7.5 Hz), 6.85 (1H, d, J 8.5 Hz). LCMS (ES$^+$) RT 3.58 minutes, 344 (M+H)$^+$.

EXAMPLE 12

6-Oxo-7-phenyl-3-phenylamino-6,7-dihydrothieno[2,3-b]pyridine-2-carboxamide

To a 100 ml round-bottomed flask, fitted with nitrogen inlet/outlet, was added Example 11 (1.45 g) and 13.3 mL of a solution of 0.382 g of NaOH in $H_2O$ (20 mL), plus absolute EtOH (30 mL). The reaction was then set to reflux. After approximately 1 hour at reflux the reaction had gone to completion. The reaction mixture was cooled to ambient, and poured onto 1M HCl (100 ml). This mixture was then extracted with DCM (2×75 mL). The combined organics were washed with 1M HCl (2×50 mL), dried ($MgSO_4$) and evaporated to dryness. The resulting crude product was then passed down a silica column eluting with 4:1 DCM:EtOAc. The product was then dried under vacuum at 50° C., to give the title compound as a light yellow solid (1.47 g). δH (DMSO-d6) 8.85 (1H, s), 7.60-7.40 (5H, m), 7.30-7.10 (5H, m), 6.80 (3H, m), 6.30 (1H, d, J 8.5 Hz). LCMS (ES$^+$) RT 2.92 minutes, 362 (M+H)$^+$.

EXAMPLE 13

3-Bromo-7-(2-chlorophenyl)-6-oxo-6,7-dihydrothieno[2,3-b]pyridine-2-carbonitrile Example 5 (1.17 g, 3.88 mmol) was suspended in MeCN (20 mL). Copper(II) bromide (953 mg, 4.27 mmol) was added, followed by tert-butyl nitrite (0.64 mL, 5.43 mmol). The mixture was stirred at r.t. for 3 h then partitioned between 2M HCl aq (100 mL) and EtOAc (100 mL). The organic layer was washed with 2M HCl aq (50 mL), 2M NaOH aq (50 mL) and water (25 mL), dried ($Na_2SO_4$) and concentrated in vacuo. Purification by column chromatography (silica, 0 to 5% EtOAc in DCM) gave the title compound as a pale brown solid (980 mg, 67%). δH ($CDCl_3$) 7.70 (1H, d, J 9.7 Hz), 7.61 (1H, dd, J 1.7, 7.7 Hz), 7.52-7.44 (2H, m), 7.34 (1H, dd, J 1.7, 7.7 Hz), 6.70 (1H, d, J 9.7 Hz). LCMS (ES$^+$) RT 3.56 minutes, 365 (M+H)$^+$.

EXAMPLE 14

7-(2-Chlorophenyl)-3-[(4-fluoro-3-methylphenyl)amino]-6-oxo-6,7-dihydrothieno[2,3-b]pyridine-2-carbonitrile A mixture of Example 13 (500 mg, 1.37 mmol), 4-fluoro-3-methylaniline (206 mg, 1.64 mmol), $Cs_2CO_3$ (625 mg, 1.92 mmol), BINAP (85 mg, 0.37 mmol, 10 mol %) and $Pd_2(dba)_3$ (63 mg, 0.0685 mmol, 5 mol %) in toluene was heated at reflux for 18 h. A second charge of BINAP (42 mg, 5 mol %) and tris(dibenzylideneacetone)dipalladium(0) (31.5 mg, 2.5 mol %) was added and the mixture heated at reflux for a further 4 days. The mixture was partitioned between DCM (100 mL) and $H_2O$ (50 mL). The organic layer was dried ($Na_2SO_4$) and concentrated in vacuo. Purification by column chromatography (silica, 10% EtOAc in DCM) gave the title compound as an off-white solid (160 mg, 28%). δH (DMSO-d6) 9.39 (1H, s), 8.17 (1H, d, J 9.7 Hz), 7.87 (1H, dd, J 1.7, 7.9 Hz), 7.79 (1H, dd, J 2.1, 7.9 Hz), 7.75-7.66 (2H, m), 7.24-7.12 (3H, m), 6.71 (1H, d, J 9.7 Hz), 2.29 (3H, d, J 1.7 Hz). LCMS (ES$^+$) RT 3.63 minutes, 410 (M+H)$^+$.

EXAMPLE 15

7-(2-Chlorophenyl)-3-[(4-fluoro-3-methylphenyl)amino]-6-oxo-6,7-dihydrothieno[2,3-b]pyridine-2-carboxamide Sodium hydroxide (0.68 mL of a 0.25M aq. solution, 0.17 mmol) was added to Example 14 (136 mg, 0.33 mmol) in ethanol (6 mL) and the mixture heated at reflux for 1 h. The mixture was concentrated in vacuo, the residue suspended in water and the solid filtered off and dried. Purification by column chromatography (silica, 20% EtOAc in DCM) gave the title compound as a pale yellow solid (65 mg, 46%). δH ($CDCl_3$) 9.08 (1H, br s), 7.60-7.57 (1H, m), 7.48-7.41 (2H, m), 7.38-7.35 (1H, m), 7.06 (1H, d, J 9.8 Hz), 6.93-6.85 (3H, m), 6.29 (1H, d, J 9.8 Hz), 5.18 (2H, br s), 2.20 (3H, d, J 1.4 Hz). LCMS (ES$^+$) RT 3.28 minutes, 428 (M+H)$^+$.

EXAMPLE 16

3-Amino-7-phenyl-2-(pyrrolidine-1-carbonyl)-7H-thieno[2,3-b]pyridin-6-one

A mixture of Example 1 (0.5 g) and Intermediate 2 (0.35 g) in MeCN (10 mL) was heated at reflux for 1.5 h. $H_2O$ (2.5 mL) was added and the resulting mixture was concentrated in vacuo. The resulting solid precipitate was recovered by filtration and dried under vacuum to give 6-oxo-2-[2-oxo-2-(pyrrolidin-1-yl)ethylsulfanyl]-1-phenyl-1,6-dihydropyridine-3-carbonitrile (0.56 g). δH (DMSO-d6) 7.998 (1H, d, J 9.5 Hz), 7.75 (3H, m), 7.55 (2H, m), 6.85 (1H, d, J 9.5 Hz), 3.86 (2H, s), 3.62-3.37 (4H, m), 2.15-1.90 (4H, m). A mixture of this material (0.38 g) and $K_2CO_3$ (0.31 g) in EtOH (7.5 mL) was heated at reflux for 2.5 h. H₂O (10 mL) was added and the mixture was concentrated under vacuum. The resulting solid product was filtered, washed with water and dried in vacuo to give the title compound as an off-white solid (0.37 g). δH (DMSO-d6) 8.12 (1H, d, J 9.4 Hz), 7.66-7.50 (3H, m), 7.44 (2H, m), 7.25 (2H, br s), 6.50 (1H, d, J 9.4 Hz), 3.36 (4H, m), 1.75 (4H, m). LCMS (ES⁺) RT 2.84 minutes, 340 (M+H)⁺.

EXAMPLE 17

7-Phenyl-3-phenylamino-2-(pyrrolidine-1-carbonyl)-7H-thieno[2,3-b]pyridin-6-one To a dry 50 ml 3-necked round-bottomed flask, fitted with nitrogen inlet/outlet, was added K₃PO₄ (94 mg), tBU₃PH.BF₄ (8.6 mg), Example 16 (100 mg) and Pd₂(dba)₃ (13.5 mg). To this mixture was added 10 ml of anhydrous DME, which had been thoroughly degassed. The reaction mixture was then put through a vacuum and nitrogen cycle. To the reaction mixture was added bromobenzene (70 mg) via syringe. The reaction was then set to reflux. After 5 hours at reflux the reaction had gone to completion. The reaction mixture was cooled to ambient, and held at this temperature for 1 hour. The reaction mixture was then poured onto HCl (20 ml, 1.0N) and extracted with DCM (2×50 ml). The combined organics were then washed with water (50 ml). The organic layer was then dried (MgSO₄) and evaporated to give the crude product quantitatively as a pale yellow solid. Recrystallisation from MeOH, and drying under vacuum at 50° C., gave the title compound as an off-white solid (50 mg). δH (CDCl₃) 9.61 (1H, s), 7.70-7.50 (3H, m), 7.45 (2H, m), 7.36 (1H, m), 7.30 (2H, m), 7.05 (3H, m), 6.41 (1H, d, J 9.7 Hz), 3.55-3.65 (4H, m), 1.85-1.95 (4H, m). LCMS (ES⁺) RT 3.55 minutes, 416 (M+H)⁺.

EXAMPLE 18

Sodium 3-cyano-1-cyclopropyl-6-oxo-1,6-dihydro-nyridine-2-thiolate

A solution of NaHMDS (122 mL of a 1.0M solution in THF, 122 mmol) was added to a solution of cyclopropyl isothiocyanate (4.85 g, 48.9 mmol) and MeCN (25.5 mL, 10 eq) in THF (50 mL) at −78° C. The mixture was allowed to warm to r.t. over 2 h. N,N-Dimethyluracil (5.9 g, 49 mmol) and EtOH (60 mL) were added and the mixture heated at reflux for 3 h then stirred at r.t. overnight. Volatiles were removed in vacuo. The residue was taken up in a mixture of EtOH and EtOAc then Et₂O was added. The sticky solid was filtered off and dried to give the title compound (11 g, crude) which was used in the next step without further purification.

EXAMPLE 19

3-Amino-7-cyclopropyl-6-oxo-6,7-dihydrothieno[2,3-b]pyridine-2-carbonitrile

A mixture of crude Example 18 (9 g, assume 42 mmol) and chloroacetonitrile (2.7 mL, 42 mmol) in MeCN (100 mL) was heated at reflux for 3 h. Volatiles were removed in vacuo. H₂O (100 mL) was added to the residue and the solid obtained filtered off and dried. The crude material was partitioned between H₂O and EtOAc and the aqueous phase extracted with EtOAc. The combined organic phases were concentrated in vacuo. The residue was dissolved in EtOH and the solution treated with Et₂O to give a solid which was filtered off and dried to give the title compound as a light brown solid (2.5 g). δH (CDCl₃) 7.42 (1H, d, J 9.6 Hz), 6.52 (1H, d, J 9.6 Hz), 4.6 (2H, br s), 3.08-3.00 (1H, m), 1.20-1.10 (2H, m), 1.08-1.00 (2H, m). LCMS (ES⁺) RT 2.532 minutes, 232 (M+H)⁺.

EXAMPLE 20

3-Bromo-7-cyclopropyl-6-oxo-6,7-dihydrothieno[2,3-b]pyridine-2-carbonitrile

Copper(II) bromide (0.53 g, 2.37 mmol) and tert-butyl nitrite (0.40 mL, 3.02 mmol) were added to a solution of Example 19 (0.5 g, 2.16 mmol) in MeCN (15 mL). The reaction mixture was stirred at r.t. for 4 h. DCM (100 mL) was added and the mixture washed with 2M HCl aq and 2M NaOH aq, dried (MgSO₄) and concentrated in vacuo to give the title compound (400 mg, 63%). δH (CDCl₃) 7.62 (1H, d, J 10.2 Hz), 6.63 (1H, d, J 10.3 Hz), 3.10-3.00 (1H, m), 1.30-1.20 (2H, m), 1.10-1.00 (2H, m). LCMS (ES⁺) RT 3.184 minutes, 296.8 (M+H)⁺.

EXAMPLE 21

7-Cyclopropyl-3-[(3-methylphenyl)amino]-6-oxo-6,7-dihydrothieno[2,3-b]pyridine-2-carbonitrile Prepared from Example 20 and m-toluidine by the method of Example 14. Light yellow solid. δH (CDCl₃) 7.25 (1H, d, J 9.6 Hz), 7.20-7.16 (1H, m), 6.04 (1H, d, J 7.6 Hz), 7.82-7.80 (2H, m), 6.67 (1H, s), 6.33 (1H, d, J 9.6 Hz), 3.07-3.02 (1H, m), 2.31 (3H, s), 1.32-1.17 (2H, m), 1.14-1.07 (2H, m). LCMS (ES⁺) RT 3.336 minutes, 321.9 (M+H)⁺.

EXAMPLE 22

7-Cyclopropyl-3-[(3-methylphenyl)amino]-6-oxo-6,7-dihydrothieno[2,3-b]pyridine-2-carboxamide Prepared from Example 21 by the method of Example 15. Light yellow solid. δH (CDCl₃) 8.65 (1H, br s), 7.25-7.11 (2H, m), 6.88 (1H, d, J 7.5 Hz), 6.83-6.80 (2H, m), 6.24 (1H, d, J 9.7 Hz), 5.68 (2H, br s), 3.08-3.05 (1H, m), 2.30 (3H, s), 1.34-1.23 (2H, m), 1.15-1.13 (2H, m). LCMS (ES⁺) RT 2.888 minutes, 340 (M+H)⁺.

EXAMPLE 23

6-Oxo-7-phenyl-3-m-tolylamino-6,7-dihydrothieno[2,3-b]pyridine-2-carbonitrile Method A To a dry 2 L jacketed vessel, fitted with nitrogen inlet/outlet, was added K₃PO₄ (120 g), 3-bromotoluene (69.7 g) and Example 3 (100.5 g). To this mixture was added 1 L of anhydrous DME. The reaction mixture was then thoroughly degassed by purging with nitrogen vigorously for approximately 1 hour. To the reaction mixture was then added tBU₃PH.BF₄ (6.57 g) and Pd₂(dba)₃ (2.59 g), washing in with DME (50 ml). The reaction was then set to reflux. After ~3 hours at reflux the reaction had gone to completion. The reaction mixture was cooled to ambient, and then poured onto 1 L of 0.1M EDTA solution. The resulting granular solid was then stirred at RT for 1 hour. The solid was then collected, by filtration washing with water (3×200 ml). The product was then dried under vacuum at 50° C., to give the title compound as a beige solid (122 g, 92.0%). HPLC indicated PAR of 92.5%, and 5.0% of the bis-arylated product. This could be further purified by recrystallisation from acetic acid to give the title compound. δH (DMSO-d6) 7.60-7.70 (3H m), 7.40 (2H m), 7.35 (1H, d, J 9.7 Hz), 7.25 (1H, m), 6.85-7.00 (3H, m), 6.50 (1H d, J 9.7 Hz), 6.40 (1H, s), 2.35 (3H, s). LCMS (ES$^+$) RT 3.85 minutes, 358.2 (M+H)$^+$.

Method B

To a dry 25 ml flask was charged $K_3PO_4$ (1.69 g), copper(I) iodide (0.08 g), ethylene glycol (0.50 g), 3-iodotoluene (1.75 g) and Example 3 (1.07 g). To this was added previously degassed anhydrous 1,4-dioxane and this mixture subjected to a vacuum/nitrogen cycle. The reaction was heated to reflux under a nitrogen atmosphere and monitored by LC. After 1.5 hours complete conversion was achieved. The reaction was then poured into water (30 ml) and extracted with DCM (30 ml). The DCM was washed with 2×30 ml 5% EDTA solution, the aqueous layers combined and extracted with 20 ml DCM. All the organics were combined, dried over sodium sulfate, filtered and concentrated under reduced pressure. The residue was slurried in 10 ml MeOH at room temperature for 2 hours, filtered, washed with MeOH (3×2 ml) and dried in vacuo to yield the title compound (0.74 g). δH (DMSO-d6) 7.60-7.70 (3H m), 7.40 (2H m), 7.35 (1H, d, J 9.7 Hz), 7.25 (1H, m), 6.85-7.00 (3H, m), 6.50 (1H d, J 9.7 Hz), 6.40 (1H, s), 2.35 (3H, s). LCMS (ES$^+$) RT 3.85 minutes, 358.2 (M+H)$^+$.

Method C

The compound of Example 3 (5.00 g), 3-iodotoluene (4.85 ml), copper(I) iodide (0.36 g), $K_3PO_4$ (7.90 g), and N,N-dimethylethanolamine (50 ml) were placed in a pre-dried 250 ml round-bottom flask fitted with a reflux condenser. The flask was sealed, then evacuated and back-filled with nitrogen three times. The white/pink suspension was stirred by the action of a magnetic stirring bar and heated to 80° C. The reaction developed into a brown suspension and then on to a brown solution. After 1.5 hours at this temperature the reaction was shown to be complete by hplc. The reaction was cooled to room temperature, quenched by the addition of 100 ml of water, and stirred for a further 1 h at room temperature. Filtration of the resultant suspension, washing with a further 100 ml of water, gave, after drying, a crude green/brown solid (6.78 g). The crude product (6.00 g) was recrystallised from 4 volumes of AcOH, washed with EtOAc (50 ml) and then dried under vacuum to give the title compound as a yellow solid (4.16 g). δH (DMSO-d6) 7.60-7.70 (3H m), 7.40 (2H m), 7.35 (1H, d, J 9.7 Hz), 7.25 (1H, m), 6.85-7.00 (3H, m), 6.50 (1H d, J 9.7 Hz), 6.40 (1H, s), 2.35 (3H, s). LCMS (ES$^+$) RT 3.85 minutes, 358 (M+H)$^+$.

EXAMPLE 24

6-Oxo-7-phenyl-3-m-tolylamino-6,7-dihydrothieno[2,3-b]pyridine-2-carboxamide

A solution of KOH (12.69 g, 85+%) in water (230 ml) was added to a suspension of Example 23 (114 g) in EtOH (345 ml). The resulting mixture was heated at reflux for 70 minutes, by which time the reaction had gone to completion. It was cooled and water (285 ml) added. The suspension was filtered and washed with water (200 ml). The product was dried under vacuum to give the title compound as a yellow solid (120 g). δH (CDCl$_3$) 8.90 (1H, s), 7.55-7.65 (3H, m), 7.40 (2H, m), 7.20-7.30 (2H, m), 6.90 (3H, m), 6.35 (1H, d, J 9 Hz), 5.40 (2H, br s), 3.70 (2H, q, EtOH), 2.35 (3H, s), 1.25 (3H, t, EtOH). LCMS (ES$^+$) RT 3.1 minutes, 376 (M+H)$^+$.

EXAMPLE 25

3-Amino-7-phenyl-2-[(R)-3-(tetrahydropyran-2-yloxy)pyrrolidine-1-carbonyl]-7H-thieno[2,3-b]pyridin-6-one A suspension of Intermediate 4 (11.6 g), Example 1 (11.75 g at 100%), and $K_2CO_3$ (6.5 g) in acetonitrile (135 ml) was heated to reflux for 2 h. The reaction was then cooled to ambient temperature, and water (270 ml) was added. The mixture was stirred for 45 minutes, then filtered. The light brown solid was washed with water, then dried in a vacuum oven at 40° C. The title compound was obtained in a 73% yield (15.1 g). δH (CDCl$_3$) 7.75 (1H, d, J 9.4 Hz), 7.50-7.75 (3H, m), 7.30-7.45 (2H, m), 6.65 (1H, d, J 9.4 Hz), 6.25 (2H, br s), 4.60-4.70 (1H, m), 4.35-4.45 (1H, m), 3.40-3.90 (6H, m), 1.40-2.20 (8H, m). LCMS (ES$^+$) RT 3.36 min, 440 (M+H)$^+$.

EXAMPLE 26

3-(4-Fluoro-3-methylphenylamino)-7-phenyl-2-[(R)-3-(tetrahydropyran-2-yloxy)pyrrolidine-1-carbonyl]-7H-thieno[2,3-b]pyridin-6-one Method A To a dry 100 ml 2-necked round-bottomed flask, fitted with nitrogen inlet/outlet, was added Example 25 (1 g), $K_3PO_4$ (0.72 g), P$^t$Bu$_3$H.BF$_4$ (0.072 g) and Pd$_2$(dba)$_3$ (0.105 g). To this mixture was added 5-bromo-2-fluorotoluene (0.517 g) as a solution in anhydrous DME (30 ml). This solution had been thoroughly degassed. The reaction mixture was then put through a vacuum and nitrogen cycle. The reaction was then set to reflux. After 21 hours at reflux the reaction had gone to approximately 98% completion. The reaction mixture was cooled to ambient, and then poured onto EDTA solution (30 ml, 5%), before filtering through celite. This was then extracted with DCM (2×30 ml). The combined organics were then washed with water (50 ml), dried over MgSO$_4$ and evaporated to give a brown oil. This was then crystallised by stirring in 3 volumes of EtOH, then dried under vacuum at 40° C., to give the title compound as a pale yellow solid (0.70 g). δH (DMSO-d6) 8.90 (1H, d, J 15 Hz), 7.67-7.50 (6H, m), 7.02-6.97 (1H, m), 6.85-6.84 (1H, m), 6.77-6.72 (1H, m), 6.49 (1H, d, J 9.5 Hz), 4.61-4.48 (1H, m), 4.19-4.15 (1H, m), 3.71-3.24 (6H, m), 2.16 (3H, s), 1.79-1.27 (8H, m). LCMS (ES$^+$) RT 4.02 minutes, 549 (M+H)$^+$.

Method B

To a dry 100 ml 3-necked round bottomed flask, fitted with nitrogen inlet/outlet, was added Example 25 (0.50 g), $K_3PO_4$ (0.484 g) and CuI (0.024 g). To this mixture was added a thoroughly degassed solution of 5-iodo-2-fluorotoluene (0.30 g) and ethylene glycol (0.141 g) in isopropanol (20 ml). The reaction mixture was then put through a vacuum and nitrogen cycle. The reaction was then set to reflux. After 26 hours at reflux the reaction had gone to approximately 85% conversion. The reaction mixture was cooled to ambient, and then poured onto, 1M HCl solution (25 ml). This was then extracted with DCM (2×50 ml). The combined organics were then washed with water (50 ml), dried over MgSO$_4$ and evaporated to give a crude brown oil. Crystallisation from 3 volumes of EtOH yielded the title compound as a pale yellow solid (0.125 g). δH (DMSO-d6) 8.90 (1H, d, J 15 Hz), 7.67-

7.50 (6H, m), 7.02-6.97 (1H, m), 6.85-6.84 (1H, m), 6.77-6.72 (1H, m), 6.49 (1H, d, J 9.5 Hz), 4.61-4.48 (1H, m), 4.19-4.15 (1H, m), 3.71-3.24 (6H, m), 2.16 (3H, s), 1.79-1.27 (8H, m). LCMS (ES$^+$) RT 3.99 minutes, 549 (M+H)$^+$.

EXAMPLE 27

3-(4-Fluoro-3-methylphenylamino)-2-((R)-3-hydroxypyrrolidine-1-carbonyl)-7-phenyl-7H-thieno[2,3-b]pyridin-6-one A suspension of Example 26 (5.8 g) in EtOH (180 ml) was treated with 1.3M HCl (32 ml). The mixture was stirred at ambient temperature overnight. The pH was adjusted to 8 using 2M sodium hydroxide. The resulting mixture was concentrated to remove the EtOH, and the solid was filtered off, washed with water, then reslurried in 25 ml water for 1 h. The suspension was filtered, washed with water, and the product was dried in a vacuum oven at 45° C. overnight. The beige solid was recrystallised from 19 volumes of EtOH, to give the title compound as a crystalline solid (3.52 g). δH (CDCl$_3$) 9.65 (s, 1H), 7.65-7.50 (3H, m), 7.35-7.50 (2H, m), 7.25 (1H, d, J 9 Hz), 6.85-7.00 (3H, m), 6.40 (1H, d, J 9 Hz), 4.50 (1H, br s), 3.55-3.80 (4H, m), 2.25 (3H, br s), 1.95-2.05 (2H, m), 1.80 (1H, d, J 4 Hz). LCMS (ES$^+$) RT 2.90 min, 464 (M+H)$^+$.

EXAMPLE 28

3-Amino-2-((S)-2-hydroxymethylpyrrolidine-1-carbonyl)-7-phenyl-7H-thieno[2,3-b]pyridin-6-one A mixture of Intermediate 5 (1.2 g), Example 1 (1.69 g at 100%) and K$_2$CO$_3$ (0.93 g) in MeCN (10 ml), was heated at reflux for 2 hours. Water (10 ml) was added and any insoluble material was removed by filtration. The resulting filtrate was concentrated under vacuum and then extracted with DCM (3×5 ml). The combined organic extracts were washed with brine (5 ml), dried over sodium sulphate and then evaporated to leave the title compound as a yellow foam (1.34 g). δH (DMSO-d6) 8.26 (1H, d, J 9 Hz), 7.80-7.65 (3H, m), 7.63-7.50 (2H, m), 7.44-7.34 (2H, m), 6.66 (1H, d, J 9 Hz), 4.80 (1H, br s), 4.25 (1H, m), 3.65-3.35 (4H, m), 2.10-1.80 (4H, m). LCMS (ES$^+$) RT 2.44 min, 370 (M+H)$^+$.

EXAMPLE 29

3-(4-Fluoro-3-methylphenylamino)-2-((S)-2-hydroxymethylpyrrolidine-1-carbonyl)-7-phenyl-7H-thieno[2,3-b]pyridin-6-one To a dry 25 ml flask fitted with nitrogen inlet/outlet was added K$_3$PO$_4$ (0.589 g), ethylene glycol (0.178 g), 2-fluoro-5-iodotoluene (0.368 g), copper(I) iodide (0.028 g) and Example 28 (0.516 g). To this was added previously degassed anhydrous propan-2-ol (10 ml). This was then subjected to a nitrogen/vacuum cycle. The reaction was then heated to reflux for 17.5 hours under a nitrogen atmosphere. After this time the reaction was filtered, and the liquors poured into water (50 ml). This was then extracted with DCM (1×30 ml and 2×20 ml), the organic layers combined and washed with 1M ammonia solution (1×100 ml) then 1M ammonia solution (1×50 ml) and water (1×50 ml). The organics were dried over sodium sulfate and concentrated to dryness under reduced pressure. The residue was then columned over silica (30 g) using DCM/EtOAc as eluent. This afforded 0.140 g of the title compound. δH (DMSO-d6) 8.74 (1H, s), 7.78-7.75 (1H, d, J 9.7 Hz), 7.65-7.61 (3H, m), 7.58-7.51 (2H, m), 7.02-6.96 (1H, t), 6.82-6.79 (1H, m), 6.76-6.72 (1H, m), 6.53-6.49 (1H, d, J 9.7 Hz), 4.63-4.60 (1H, t), 3.89 (1H, broad), 3.28-3.21 (3H, m), 2.80-2.78 (1H, m), 2.14 (3H, s), 1.71-1.51 (4H, m). LCMS ES$^+$ RT 3.29 min, 478.0 (M+H)$^+$.

EXAMPLE 30

3-Bromo-6-oxo-7-phenyl-6,7-dihydrothieno[2,3-b]pyridine-2-carboxyic acid ethyl ester tert-Butyl nitrite (90% technical grade, 10 ml) and copper (II) bromide (16.66 g) were stirred in MeCN (200 ml) in a 1 l jacketed vessel at 10° C. under nitrogen. To this cooled mixture was added Example 4 (20 g) in ~1 g portions over 90 min. After a further hour at 10° C. the reaction was allowed to warm to room temperature. The reaction mixture was poured onto 300 ml of 1M HCl and stirred for 30 min (CAUTION: brown fumes). The resultant green suspension was filtered to give a crude orange solid which was washed with water (2×200 ml). Recrystallisation of the crude solid from 7 volumes of MIBK gave the title compound as a yellow/orange solid (17.81 g). δH (DMSO-d6) 7.90 (1H, d, J 10 Hz), 7.50-7.70 (5H, m), 6.90 (1H, d, J 10 Hz), 4.25 (2H q, J 7 Hz), 1.25 (3H, t, J 7 Hz). LCMS (ES$^+$) RT 3.78 minutes, (M)$^+$ 378.

EXAMPLE 31

3-Amino-2-nitro-7-phenyl-7H-thieno[2,3-b]pyridine-6-one

To 36.6 g of Example 1 was added 400 ml of acetonitrile. The resulting suspension was heated to 70° C. and 22.5 g bromonitromethane was added dropwise over 20 minutes. The reaction was heated at reflux for a further 100 minutes before cooling in an ice bath. The resultant precipitate was isolated by suction and washed well with water. After drying under vacuum at 55° C., a yield of 35.9 g of the title compound was obtained. δH (DMSO-d6) 6.60 (1H, d, J 9.4 Hz), 7.50 (2H, m), 7.62 (3H, m), 8.25 (1H, d, J 9.4 Hz). LCMS (ES$^+$) RT 2.64 minutes, 288 (M+H)$^+$.

EXAMPLE 32

3-Bromo-2-nitro-7-phenyl-7H-thieno[2,3-b]pyridine-6-one

To a 500 ml flask was added 350 ml of acetonitrile. With stirring under a nitrogen atmosphere was added tert-butyl nitrite (15.1 g) and copper(II) bromide (29.9 g). The resulting mixture was cooled to 6° C. and Example 31 (35 g) was added in portions over 4 hours, while maintaining the temperature below 10° C. The reaction was then allowed to warm to ambient temperature and stirred for 16 hours. The reaction mixture was poured into 280 ml of 2M hydrochloric acid and the product obtained by suction, washing with water. After drying, the crude product was purified by silica gel chromatography to give the title compound as a yellow powder (24.6 g). δH (DMSO-d6) 6.80 (1H, d, J 9.4 Hz), 7.59 (2H, m), 7.68 (3H, m), 7.98 (1H, d, J 9.4 Hz). LCMS (ES$^+$) RT 3.54 minutes, 351 (M+H)$^+$.

EXAMPLE 33

3-Amino-2-(4-ethylpiperazin-1-ylcarbonyl)-7-phenyl-7H-thieno[2,3-b]pyridin-6-one A mixture of Intermediate 6 (1.5 g), Example 1 (1.97 g at 100%) and $K_2CO_3$ (1.09 g) in acetonitrile (50 ml) was heated at reflux for 6 hours and then cooled to room temperature. Water (50 ml) was added and the reaction stirred for 30 min at room temperature. The mixture was extracted with DCM (2×100 ml) and the organic layer was dried ($MgSO_4$) and concentrated in vacuo. Purification by column chromatography (silica, 5% MeOH in DCM) gave the title compound as a dark brown solid (1.58 g, 53%). δH ($CDCl_3$) 7.58 (4H, m), 7.39 (2H, m), 6.63 (1H, d, J 9.5 Hz), 5.70 (2H, s), 3.65 (4H, m), 2.42 (6H, m), 1.08 (3H, t, J 7.2 Hz). LCMS ($ES^+$) RT 1.33 minutes, 383 $(M+H)^+$.

EXAMPLE 34

3-Bromo-2-(4-ethylpiperazin-1-ylcarbonyl)-7-phenyl-7H-thieno[2,3-b]pyridin-6-one Example 33 (1.3 g) in acetonitrile (50 ml) was added dropwise as a slurry to copper(II) bromide (1.1 g) and tert-butyl nitrite (0.40 ml) in acetonitrile (10 ml) at 10° C. The mixture was stirred at room temperature for 2 hours then concentrated in vacuo to leave a dark brown oil which was stirred overnight in DCM (100 ml) and 2M HCl (100 ml). The organic layer was dried ($MgSO_4$) and concentrated in vacuo. Purification by column chromatography (silica, 5% MeOH in DCM) gave the title compound as a yellow oil (400 mg, 30%). δH ($CDCl_3$) 7.74 (1H, d, J 9.3 Hz), 7.60 (3H, m), 7.39 (2H, m), 6.73 (1H, d, J 9.1 Hz), 4.10 (4H, m), 3.10 (6H, m), 1.45 (3H, m). RT 1.48 minutes, 446, 448 $(M+H)^+$.

EXAMPLE 35

2-(4-Ethylpiperazin-1-ylcarbonyl)-7-phenyl-3-phenylamino-7H-thieno[2,3-b]pyridin-6-one To a dry 100 ml flask was charged $Cs_2CO_3$ (411 mg), (+/−)-BINAP (56 mg), $Pd_2(dba)_3$ (catalytic amount), aniline (92 mg) and Example 34 (400 mg). To this was added 20 ml of previously degassed toluene. This mixture was then subjected to a vacuum/nitrogen cycle. The reaction was then heated to reflux under a nitrogen atmosphere. LCMS analysis after ~8 h showed 47% conversion to the title compound. RT 1.83 minutes, 459 $(M+H)^+$.

The invention claimed is:

1. A compound of formula (2):

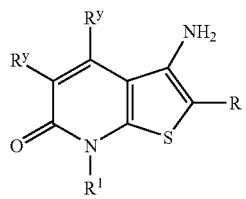

(2)

wherein R is a —CN, —$NO_2$, —$CO_2Alk^2$, —$COC_{1-6}$alkyl or —$CONHet^2$ group;

$Alk^2$ is an optionally substituted alkyl, arylalkyl, aryl, aryloxyalkyl, alkanoyloxyalkyl or aroyloxyalkyl group;

$NHet^2$ is an optionally substituted 4- to 6-membered heterocycloalkyl group attached through a nitrogen atom to the group —CO;

$R^1$ is an optionally substituted aryl, heteroaryl, cycloalkyl or heterocycloalkyl group; and each $R^y$, which may be the same or different, is each a hydrogen atom or a hydrogen atom precursor;

or a salt, protected derivative, or N-oxide thereof.

2. A compound according to claim 1 in which $R^1$ is an optionally substituted phenyl, pyridyl, pyrimidinyl, pyridazinyl, pyrazinyl, thienyl, indolyl, cyclopropyl, cyclobutyl, cyclopentyl or cyclohexyl group.

3. A compound according to claim 2 wherein $R^1$ is an optionally substituted phenyl or cyclopropyl group.

4. A compound according to claim 1 in which each $R^y$ is a hydrogen atom.

5. A compound according to claim 1 in which $Alk^2$ is a $C_{1-6}$ alkyl group.

6. A compound according to claim 1 wherein R is a —CN, —$CO_2CH_3$, —$CO_2CH_2CH_3$, —$COCH_3$ or —$CONHet^2$ group.

7. A process for the manufacture of a compound of formula (1):

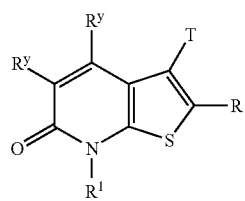

(1)

wherein R is a —CN, —$NO_2$, —$CO_2Alk^2$, —$COC_{1-6}$alkyl or —$CONHet^2$ group;

$Alk^2$ is an optionally substituted alkyl, arylalkyl, aryl, aryloxyalkyl, alkanoyloxyalkyl or aroyloxyalkyl group;

$NHet^2$ is an optionally substituted 4- to 6-membered heterocycloalkyl group attached through a nitrogen atom to the group —CO;

$R^1$ is an optionally substituted aryl, heteroaryl, cycloalkyl or heterocycloalkyl group;

each $R^y$, which may be the same or different, is a hydrogen atom or a hydrogen atom precursor; and T is a halogen atom;

which comprises diazotization of a compound of formula (2)

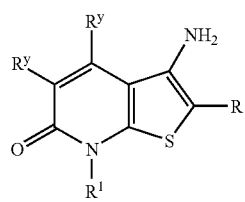

(2)

followed by halide displacement.

8. A process according to claim 7 wherein the reaction is carried out in the presence of an alkyl nitrite or a metal nitrite in the presence of an acid, followed by addition of a copper salt, in the presence of a solvent.

9. A process for the manufacture of a compound of formula (1A):

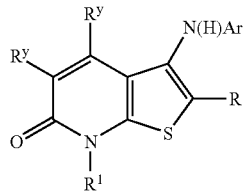
(1A)

wherein R is a —CN, —NO$_2$, —CO$_2$Alk$^2$, —COC$_{1-6}$alkyl or —CONHet$^2$ group;

Alk$^2$ is an optionally substituted alkyl, arylalkyl, aryl, aryloxyalkyl, alkanoyloxyalkyl or aroyloxyalkyl group;

NHet$^2$ is an optionally substituted 4- to 6-membered heterocycloalkyl group attached through a nitrogen atom to the group —CO;

R$^1$ is an optionally substituted aryl, heteroaryl, cycloalkyl or heterocycloalkyl group;

each R$^y$, which may be the same or different, is a hydrogen atom or a hydrogen atom precursor; and Ar is an optionally substituted aromatic or heteroaromatic group;

which comprises reacting a compound of formula (2):

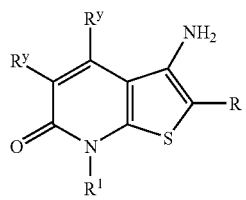
(2)

with a compound ArQ,
wherein Q is a leaving group,
in the presence of a transition metal catalyst.

10. A process according to claim 9 wherein the reaction is carried out in the presence of a solvent, using a palladium catalyst, a phosphine ligand and a base.

11. A process according to claim 9 wherein the reaction is carried out in the presence of a copper catalyst.

12. A process for the manufacture of a compound of formula (2):

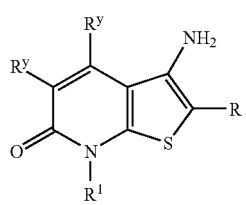
(2)

wherein R is a —CN, —NO$_2$, —CO$_2$Alk$^2$, —COC$_{1-6}$alkyl or —CONHet$^2$ group;

Alk$^2$ is an optionally substituted alkyl, arylalkyl, aryl, aryloxyalkyl, alkanoyloxyalkyl or aroyloxyalkyl group;

NHet$^2$ is an optionally substituted 4- to 6-membered heterocycloalkyl group attached through a nitrogen atom to the group —CO;

R$^1$ is an optionally substituted aryl, heteroaryl, cycloalkyl or heterocycloalkyl group;

each R$^y$, which may be the same or different, is a hydrogen atom or a hydrogen atom precursor;

which comprises the steps of:

a) reacting a compound of formula (2a) or (2b):

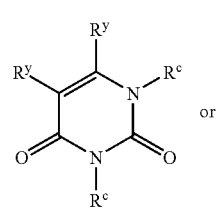
(2a)

or

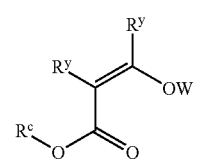
(2b)

wherein R$^c$ is an optionally substituted alkyl group, and
W is a hydrogen atom, a metal ion or an amine salt;
with a compound of formula (3):

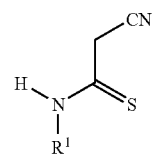
(3)

b) followed by reaction with a compound of formula (5):

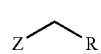
(5)

wherein Z is a leaving group.

13. The process according to claim 12 wherein W is a metal ion.

14. The process according to claim 12 wherein step a) is performed in the presence of a base.

15. The process according to claim 14 wherein the base is selected from a lithium base, a silazane, a carbonate, an alkoxide, a hydroxide, a hydride, an organic amine, and a cyclic amine.

16. The process according to claim 12 wherein the reaction is carried out in an organic solvent.

17. The process according to claim 16 wherein step a) and step b) are each carried out in an organic solvent, which may be the same or different in each step, selected from an amide, an ether, an alcohol and acetonitrile.

18. The process according to claim 12 wherein an intermediate of formula (4) is isolated after step a):

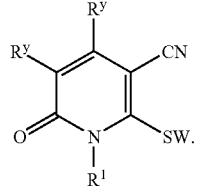
(4)

19. A compound of formula (4):

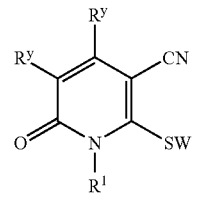
(4)

wherein $R^1$ is an optionally substituted aryl, heteroaryl, cycloalkyl or heterocycloalkyl group;
each $R^y$, which may be the same or different, is a hydrogen atom or a hydrogen atom precursor; and
W is a hydrogen atom, a metal ion or an amine salt.

20. The process according to claim 12 wherein an intermediate of formula (6) is isolated during step b):

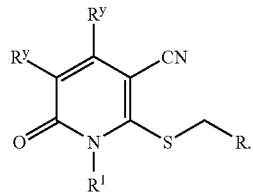
(6)

21. A compound of formula (6):

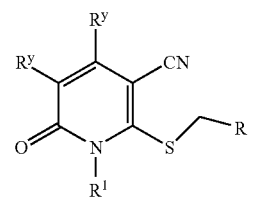
(6)

wherein R is a —CN, —$NO_2$, —$CO_2Alk^2$, —$COC_{1-6}$alkyl or —$CONHet^2$ group;
$Alk^2$ is an optionally substituted alkyl, arylalkyl, aryl, aryloxyalkyl, alkanoyloxyalkyl or aroyloxyalkyl group;
$NHet^2$ is an optionally substituted 4- to 6-membered heterocycloalkyl group attached through a nitrogen atom to the group —CO;
$R^1$ is an optionally substituted aryl, heteroaryl, cycloalkyl or heterocycloalkyl group; and
each $R^y$, which may be the same or different, is a hydrogen atom or a hydrogen atom precursor.

* * * * *